US006645490B2

United States Patent
Yarkoni et al.

(10) Patent No.: US 6,645,490 B2
(45) Date of Patent: Nov. 11, 2003

(54) CHIMERIC PROTEINS WITH CELL-TARGETING SPECIFICITY AND APOPTOSIS-INDUCING ACTIVITIES

(75) Inventors: Shai Yarkoni, Kfar-Saba (IL); Ahmi Ben-Yehudah, D.N. Harpi Yehuda (IL); Yehudith Azar, Jerusalem (IL); Rami Ishaq Aqeilan, Jerusalem (IL); Ruth Belostotsky, Maale Adumim (IL); Haya Lorberboum-Galski, Jerusalem (IL)

(73) Assignee: Yissum Research Development Company of the Hebrew University of Jerusalem, Jerusalem (IL)

( * ) Notice: Subject to any disclaimer, the term of this patent is extended or adjusted under 35 U.S.C. 154(b) by 0 days.

(21) Appl. No.: 09/033,525

(22) Filed: Mar. 2, 1998

(65) Prior Publication Data

US 2002/0090374 A1 Jul. 11, 2002

(51) Int. Cl.$^7$ ............... A61K 39/395; A61K 39/40; A61K 39/42; A61K 39/44; A01N 37/18
(52) U.S. Cl. ............... 424/134.1; 424/178.1; 514/2; 530/350; 530/351; 530/391.7; 530/391.9; 530/399
(58) Field of Search ............... 530/350, 351, 530/387.1, 300–316, 391.7, 391.9, 397, 398, 399; 424/134.1, 178.1, 179.1, 180.1; 514/2, 12

(56) References Cited

U.S. PATENT DOCUMENTS

| | | | |
|---|---|---|---|
| 4,215,051 A | | 7/1980 | Smith et al. |
| 5,602,095 A | * | 2/1997 | Pastan et al. |
| 5,759,782 A | * | 6/1998 | Pastan et al. |
| 5,834,234 A | * | 11/1998 | Gallo |
| 6,172,213 B1 | * | 1/2001 | Lowman et al. |
| 6,218,363 B1 | * | 4/2001 | Baserga et al. |

FOREIGN PATENT DOCUMENTS

| | | | |
|---|---|---|---|
| WO | WO 96/06116 | * | 2/1996 |
| WO | WO 96/38571 | | 12/1996 |
| WO | WO 97/12632 | | 4/1997 |
| WO | WO 97/19179 | | 5/1997 |
| WO | WO 97/22364 | | 6/1997 |
| WO | WO 99/45128 | | 9/1999 |

OTHER PUBLICATIONS

Lorberbaum–Galski et al. J. Biol. Chem. 265(27): 16311, 1990.*
Bargou et al. J. Clin. Invest. 97(11): 2651, Jun. 1996.*
Boyd et al. Oncogene. 11: 1921, 1995.*
Chittenden (The EMBO J.) 14(22): 5589, 1995.*
Male, D. Immunology, An Illustrated Outline. CV Mosby Co, Gower Med Publ. New York, 1986.*
Godeau et al. J. Biol. Chem, 267: 24223, 1992.*
Lorberbaum–Galsi et al. Proc. Natl. Acad. Sci. USA. 85: 1922, 1988.*

Reed JC, 1997. "Bcl–2 Family Proteins: Regulators of Apoptosis and Chemoresistance in Hematologic Malignancies." Semin. Hematol. 34 (Suppl. 5): 9–19.

Zha et al., 1996. "Proapoptotic Protein Bax Heterodimerizes with Bcl–2 and Homodimerizes with Bax via a Novel Domain (BH3) Distinct from BH1 and BH2." J. Biol. Chem. 271:7440–7444.

Antonsson et al., 1997, "Inhibition of Bax channel–forming activity by Bcl–2", Science 277:370–372.

Bailon et al., 1988, "Purification and partial characterization of an interleukin 2–Pseudomonas exotoxin fusion protein", Biotechnol. 6:1326–1329.

Becker et al., 1997, "Immunologic tolerance to myelin basic protein decreases stroke size after transient focal cerebral ischemia", Proc. Natl. Acad. Sci. USA 94:10873–10878.

Beraud et al., 1991, "Immunospecific suppression of encephalitogenic–activated T lymphocytes by chimeric cytotoxin IL–2–PE40", Cell. Immunol. 133:379–389.

Bird et al., 1988, "Single–chain antigen–binding proteins", Science 242:423–426.

Boise et al., 1993, "bcl–x, a bcl–2–related gene that functions as a dominant regulator of apoptotic cell death", Cell 74:597–608.

Brousset et al., 1996, "Frequent expression of the cell death–inducing gene Bax in Reed–Sternberg cells of Hodgkin's disease", Blood 87:2470–2475.

Case et al., 1989, "Chimeric cytotoxin IL2–PE40 delays and mitigates adjuvant–induced arthritis in rats", Proc. Natl. Acad. Sci. USA 86:287–291.

Chittenden,et al., 1995, "Induction of apoptosis by the Bcl–2 homologue Bak", Nature 374:733–736.

Chittenden,et al., 1995, "A conserved domain in Bak, distinct from BH1 and BH2, mediates cell death and protein binding functions", EMBO J. 14:5589–5596.

Cohen, 1997, "Caspases: the executioners of apoptosis", Biochem. J. 326:1–16.

Diaz et al., 1997, "A common binding site mediates heterodimerization and homodimerization of Bcl–2 family members", J. Biol. Chem. 272:11350–11355.

Fang et al., 1994, "Cloning and molecule characterization of mouse bcl–x in B and T lymphocytes", J. Immunol. 153:4388–4398.

(List continued on next page.)

Primary Examiner—Patricia A. Duffy
(74) Attorney, Agent, or Firm—Pennie & Edmonds LLP

(57) ABSTRACT

The present invention relates to chimeric proteins with cell-targeting specificity and apoptosis-inducing activities. In particular, the invention is illustrated by a recombinant chimeric protein between human interleukin-2 (IL2) and Bax. The chimeric protein specifically targets IL2 receptor (IL2R)-expressing cells and induces cell-specific apoptosis.

12 Claims, 15 Drawing Sheets

OTHER PUBLICATIONS

Figure 1:
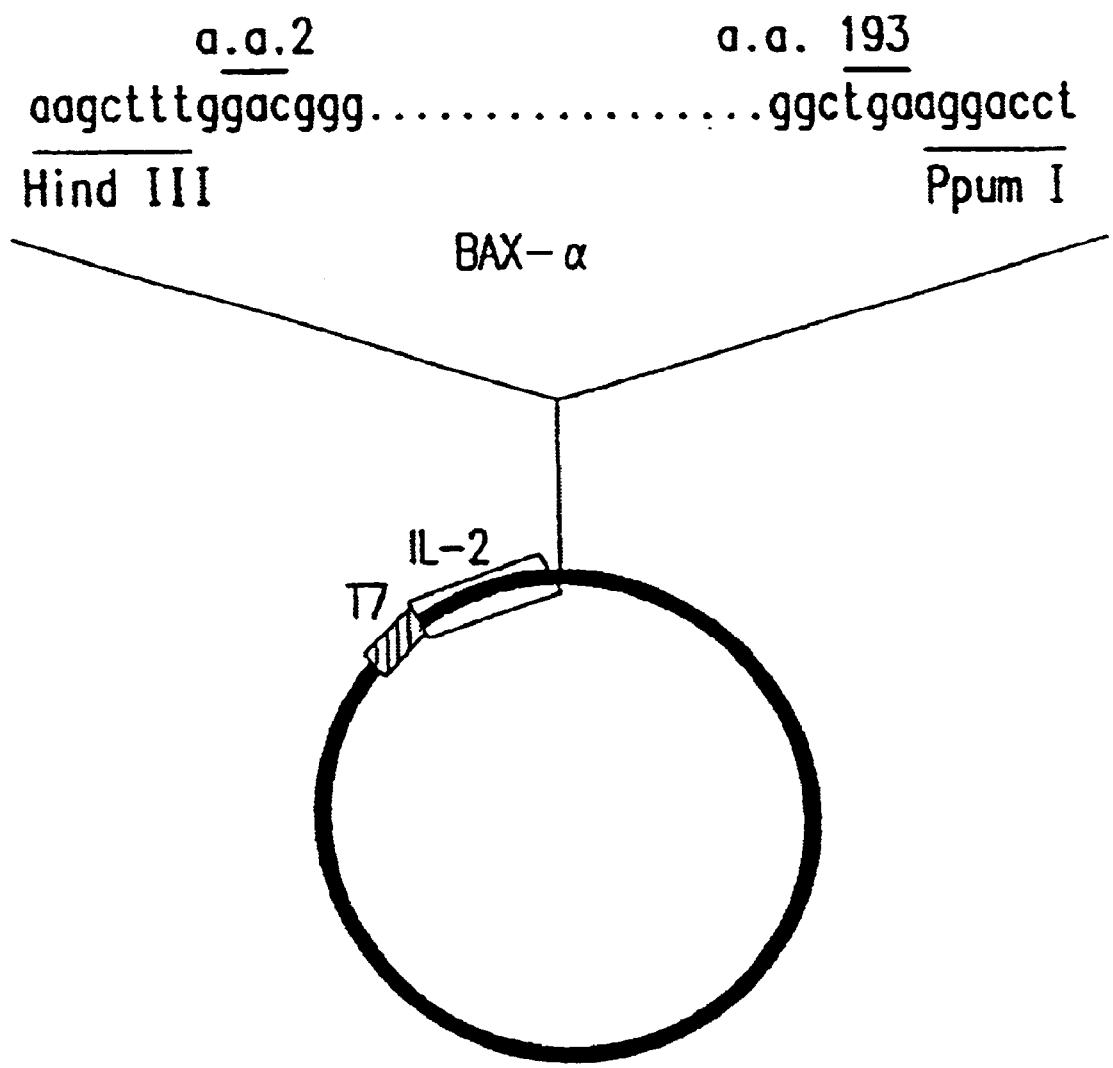

Farrow et al., 1995, "Cloning of a bcl–2 homologue by interaction with adenovirus E1B 19K", Nature 374:731–733.

Fishman et al., 1994, "Increased cytotoxicity of interleukin 2–pseudomonas exotoxin (IL2–PE) chimeric proteins containing a targeting signal for lysosomal membranes", Biochemistry 33:6235–6243.

Gazzaniga et al., 1996, "Bcl–2/bax mRNA expression ratio as prognostic factor in low–grade urinary bladder cancer", Int. J. Cancer 69:100–104.

Han et al., 1996, "Induction of apoptosis by human Nbk/Bik, a BH3–containing protein that interacts with E1B 19K", Mol. Cell. Biol. 16:5857–5864.

Helm et al., 1988, "The mast cell binding site on human immunoglobulin E", Nature 331:180–183.

Herbort et al., 1991, "Treatment of corneal allograft rejection with the cytotoxin IL–2–PE40", Transplant. 52:470–474.

Hsu et al., 1997, "Bok is a pro–apoptotic Bcl–2 protein with restricted expression in reproductive tissues and heterodimerizes with selective anti-apoptotic Bcl–2 family members", Proc. Natl. Acad. Sci. USA 94:12401–12406.

Huston et al., 1988, "Protein engineering of antibody binding sites: recovery of specific activity in an anti-digoxin single-chain Fv analogue produced in *Escherichia coli*", Proc. Natl. Acad. Sci. USA 85:5879–5883.

Inohara et al., 1997, "harakiri, a novel regulator of cell death, encodes a protein that activates apoptosis and interacts selectively with survival–promoting proteins Bcl–2 and Bcl–$X_L$", EMBO J. 16:1686–1694.

Kiefer et al., 1995, "Modulation of apoptosis by the widely distributed Bcl–2 homologue Bak", Nature 374:736–739.

Knudson and Korsmeyer, 1997, "Bcl–2 and Bax function independently to regulate cell death", Nature Genetics 16:358–363.

Kochi and Collier, 1993, "DNA fragmentation and cytolysis in U937 cells treated with diphtheria toxin or other inhibitors of protein synthesis", Exp. Cell Res. 208:296–302.

Kozak et al., 1990, "IL–2–PE40 prevents the development of tumors in mice injected with IL–2 receptor expressing EL4 transfectant tumor cells", J. Immunol. 145:2766–2771.

Kozopas et al., 1993, "MCL1, a gene expressed in programmed myeloid cell differentiation, has sequence similarity to BCL2", Proc. Natl. Acad. Sci. USA 90:3516–3520.

Krajewski et al., 1996, "Immunohistochemical analysis of in vivo patterns of Bak expression, a proapoptotic member of the Bcl–2 protein family", Cancer Res. 56:2849–2855.

Lin et al., 1993, "Characterization of A1, a novel hemopoietic-specific early–response gene with sequence similarity to bcl–2", J. Immunol. 151:1979–1988.

Liu et al., 1996, "Induction of apoptotic program in cell–free extracts: requirement for dATP and cytochrome c", Cell 86:147–157.

Lorberboum–Galski et al., 1989, "Cardiac allograft survival in mice treated with IL–2–PE40", Proc. Natl. Acad. Sci. USA 86:1008–1012.

Lorberboum–Galski et al., 1988, "Cytotoxic activity of an interleukin 2–Pseudomonas exotoxin chimeric protein produced in *Escherichia coli*", Proc. Natl. Acad. Sci. USA 85:1922–1926.

Lorberboum–Galski et al., 1988, "Interleukin 2 (IL2) PE40 is cytotoxic to cells displaying either the p55 or p70 subunit of the IL2 receptor", J. Biol. Chem. 263:18650–18656.

Moss et al., 1996, "Increased intestinal Bak expression results in apoptosis", Biochem. Biophys. Res. Comm. 223:199–203.

Nechushtan et al., 1997, "Adenocarcinoma cells are targeted by the new GnRH–$PE_{66}$ chimeric toxin through specific gonadotropin–releasing hormone binding sites", J. Biol. Chem. 272:11597–11603.

Ogata et al., 1988, "IL–2–PE40 is cytotoxic for activated T lymphocytes expressing IL–2 receptors", J. Immunol. 141:4224–4228.

Oltvai et al., 1993, "Bcl–2 heterodimerizes in vivo with a conserved homolog, Bax, that accelerates programmed cell death", Cell 74:609–619.

Ottilie et al., 1997, "Dimerization properties of human BAD. Identification of a BH–3 domain and analysis of its binding to mutant BCL–2 and BCL–$X_L$ proteins", J. Biol. Chem. 272:30866–30872.

Roberge et al., 1989, "Selective immunosuppression of activated T cells with the chimeric toxin IL–2–PE40. Inhibition of experimental autoimmune uveoretinitis", J. Immunol. 143:3498–3502.

Rose et al., 1991, "Chimeric cytotoxin IL2–PE40 inhibits relapsing experimental allergic encephalomyelitis", J. Neuroimmunol. 32:209–217.

Rüther and Müller–Hill, 1983, "Easy identification of cDNA clones", EMBO J. 2:1791–1794.

Schendel et al., 1997, "Channel formation by antiapoptotic protein Bcl–2", Proc. Natl. Acad. Sci USA 94:5113–5118.

Smith et al., 1983, "Engineering of the *Autographa californica* nuclear polyhedrosis virus genome deletion mutations within the polyhedrin gene", J. Virol. 46:584–593.

Vaux et al., 1988, "Bcl–2 gene promotes haemopoietic cell survival and cooperates with c–myc to immortalize pre–B cells", Nature 335:440–442.

Wang et al., 1996, "BID: a novel BH3 domain–only death agonist", Genes Dev. 10:2859–2869.

Williams et al., 1987, "Diphtheria toxin receptor binding domain substitution with interleukin–2: genetic construction and properties of a diphtheria toxin–related interleukin–2 fusion protein", Protein Eng. 1:493–498.

Yang et al., 1995, "Bad, a heterodimeric partner for Bcl–$X_L$ and Bcl–2, displaces Bax and promotes cell death", Cell 80:285–291.

Zha et al., 1997, "BH3 domain of BAD is required for heterodimerization with BCL–$X_L$ and pro–apoptotic activity", J. Biol. Chem. 272:24101–24104.

* cited by examiner

1/1
atg gca gat cct act tca agt tct aca aag aca cag cta caa ctg gag cat tta ctg
Met ala asp pro thr ser ser thr lys thr gln leu gln leu glu his leu leu
61/21                                    31/11
ctg gat tta cag atg att ttg aat gga att aat tac aag aat ccc aaa ctc acc agg
leu asp leu gln met ile leu asn gly ile asn tyr lys asn pro lys leu thr arg
121/41                                         91/31
atg ctc aca ttt aag ttt tac atg ccc aag aag gcc aca gaa ctg aaa cat ctt cag tgt
met leu thr phe lys phe tyr met pro lys lys ala thr glu leu lys his leu gln cys
181/61                                              151/51
cta gaa gaa ctc aaa cct ctg gag gaa gtg cta aat tta gct caa agc aaa aac ttt
leu glu glu leu lys pro leu glu glu val leu asn leu ala gln ser lys asn phe
241/81                                                   211/71
cac tta aga ccc agg gac tta atc aac aat atc agc aat leu asn val ile val leu glu leu lys gly
his leu arg pro arg asp leu ile asn val ile asn ile ser asn val ile val leu glu leu lys gly
301/101                                                       271/91
tct gaa aca aca ttc atg tgt gaa tat gct gat gag aca gca acc att gta gaa cta aag gga ttt ctg
ser glu thr thr phe met cys glu tyr ala asp glu thr ala thr ile val glu leu lys gly phe leu
361/121                                                            331/111
aac aga tgg att acc ttt tgt caa agc atc tca aca atc ccc gag ggc gaa gct ttg
asn arg trp ile thr phe cys gln ser ile ser thr ile pro glu gly glu ala leu
421/141                                                                 391/131
GAC GGG TCC GGG GAG CAG CCC AGA GGC GGG CCC ACC AGC TCT CAG CAG ATC ATG AAG
asp gly ser gly glu gln pro arg gly gly pro thr ser ser gln gln ile met lys
481/161                                                                      451/151
ACA GGG GCC CTT TTC CTT CAG GGT TTC ATC CAG GAT CGA GCA GAT CGA GCA GGG CGA ATC GGG GGG GAC
thr gly ala leu leu phe gln gly phe ile gln asp arg ala gly arg met gly gly glu
                                                                                  511/171

FIG.2A

```
541/181
GCA CCC GAG CTG GCC CTC GAC CCG GTG CCT CAG GAT GCC TCC ACC AAG AAG CTG AGC GAG
ala pro glu leu ala leu asp pro val pro gln asp ala ser thr lys lys leu ser glu
601/201                                                            631/211
TGT CTC AAG CGC ATC GGG GAC GAA CTG GAC AGT AAC ATG GAG CTG CAG AGG ATG ATT GCC
cys leu lys arg ile gly asp glu leu asp ser asn met glu leu gln arg met ile ala
661/221                                                            691/231
GCC GTG GAC ACA GAC TCC CCC CGA GAG GTC TTT TTC CGA GTG GCA GCT GAC ATG TTT TCT
ala val asp thr asp ser pro arg glu val phe phe arg val ala ala asp met phe ser
721/241                                                            751/251
GAC GGC AAC TTC AAC TGG GGC CGG GTT GTC GCC CTT TTC TAC TTT GCC AGC AAA CTG GTG
asp gly asn phe asn trp gly arg val val ala leu phe tyr phe ala ser lys leu val
781/261                                                            811/271
CTC AAG GCC CTG TGC ACC AAG GTG CCG GAG CTG ATC AGA ACC ATC ATG GGC TGG ACA TTG
leu lyb ala leu cys thr lys val pro glu leu ile arg thr ile met gly trp thr leu
841/281                                                            871/291
GAC TTC CTC CGG GAG CGG CTG TTG GGC ATC CAA GAC CAG GGT GGT TGG GAC GGC CTC
asp phe leu arg glu arg leu leu gly ile gln asp gln gly gly trp asp gly leu
901/301                                                            931/311
CTC TCC TAC TTT GGG ACG CCC ACG TGG CAG ATC TTT GTG GCC GGA GTG CTC
leu ser tyr phe gly thr pro thr trp gln thr val ile phe val ala gly val leu
961/321                                                            991/331
ACC GCC TCC CTC ACC ATC TGG AAG AAC ATG GGC TGA
thr ala ser leu thr ile trp lys lys met gly QPA
```

FIG.2B

CHIMERIC PROTEINS WITH CELL-TARGETING SPECIFICITY AND APOPTOSIS-INDUCING ACTIVITIES

1. INTRODUCTION

The present invention relates to chimeric proteins with cell-targeting specificity and apoptosis-inducing activities. In particular, the invention is illustrated by a recombinant chimeric protein between human interleukin-2 (IL2) and Bax. The chimeric protein specifically targets IL2 receptor (IL2R)-expressing cells and induces cell-specific apoptosis. In accordance with the invention, chimeric proteins may be generated between any molecule that binds a specific cell type and an apoptosis-inducing protein. Such chimeric proteins are useful for selectively eliminating specific cell types in vitro and in vivo, and may be used in the treatment of autoimmunity, cancer and infectious diseases such as viral infections.

2. BACKGROUND OF THE INVENTION

2.1. IMMUNOTOXINS

The advent of the monoclonal antibody technology and recombinant DNA technology have led to the discovery of numerous cell surface molecules associated with specific cell populations. Based on the expression pattern of these molecules, recombinant immunotoxins have been constructed to specifically target and destroy the cells that express such molecules. Recombinant immunotoxins are a class of targeted molecules designed to recognize and specifically destroy cells expressing specific receptors, such as cancer cells and cells involved in many disorders of the immune system. Generally, immunotoxins utilize a bacterial or plant toxin to destroy the unwanted cells. These molecules are designed and constructed by gene fusion techniques and are composed of both the cell targeting and cell killing moieties, a combination that makes these agents potent molecules for treatment. Examples of immunotoxins are growth factors or antigen-binding domains of antibody, including the Fv portion of an antibody (single-chain immunotoxins) fused to various mutant forms of toxin molecules. However, over the years it has become clear that treatment with such "magic bullets" for targeted immunotherapy possesses still many problems and new approaches are needed to produce improved recombinant immunotoxins.

Each recombinant immunotoxin displays some nonspecific toxicity and at sufficiently high concentrations damages normal cells that do not express the specific target antigen. This non-specific toxicity of immunotoxins is the dose-limiting factor in immunotoxin therapy. Which tissues are affected by nonspecific toxicity is dependent on the particular toxin used for immunotoxin preparation, and the ability of immunotoxins to penetrate into tissues and tumors is largely dependent on the size of the immunotoxins.

Large stable conjugated immunotoxins persist for long periods in blood vessels ($T_{1/2}$ 5–15 hour), thus endothelial cells are exposed to high toxin concentrations which may lead to endothelial cell damage. Smaller molecules, such as recombinant immunotoxins which rapidly leave the vascular system, would presumably have different toxicity. In humans, immunotoxins made with ricin and other ribotoxins, as well as with Pseudomonas exotoxin A (PE), Diphtheria toxin (DT) and their truncated derivatives have produced a variety of toxicities. These include vascular leak syndrome (mainly ricin immunotoxins) as well as liver toxicity (PE-derived immunotoxins). Vascular leak syndrome observed with ricin immunotoxins in animals and man may be explained by specific binding of ricin A-chain to endothelial cells and subsequent killing of the cells and damage to the vessels. The nonspecific liver-toxicity of PE immunotoxins is likely to be due to easy access and very rapid nonspecific uptake and internalization of proteins by hepatocytes. However, it is also possible that PE contains, in addition to the specific cell-binding site (Domain I) which is removed in most immunotoxins, an additional site which could be recognized with low affinity by hepatocytes, thus accounting for liver toxicity.

Another major impediment with immunotoxins in their clinical application is the human immune response against them, mainly toward the toxin moiety. Bacterial toxins like PE and DT are highly immunogenic and cannot be humanized with standard techniques. Usage of DT-derived immunotoxins is limited because most people in developed countries have been vaccinated against DT and many adults have neutralizing antibodies to DT. Immunogenicity is a problem to which so far no practical solution has been found. Reduced immunogenicity of these molecules would greatly improve the clinical application of immunotoxins.

An example of the successful use of an immunotoxin is the elimination of activated T cells which express high affinity IL2 receptors (IL2R), whereas normal resting T cells and their precursors do not. An immunotoxin made of IL2 could theoretically eliminate IL2R-expressing leukemia cells or IL2R-expressing immune cells involved in various disease states while not destroying IL2R negative normal cells, thereby preserving the full repertoire of antigen receptors required for T cell immune responses.

A chimeric protein, IL2-PE40, was produced and shown to eliminate activated T cells (Lorberboum-Galski et al., 1988, Proc. Natl. Acad. Sci. U.S.A. 85:1922). IL2-PE40 was extremely cytotoxic to IL2R-expressing cell lines of human, ape and murine origin. It was also extremely cytotoxic to Con A-stimulated mouse and rat spleen cells, and had a suppressive effect against antigen-activated mouse cells and the generation of cytotoxic T cells in mixed lymphocyte cultures (Lorberboum-Galski et al., 1988, J. Biol. Chem. 263:18650–18656; Ogata et al., 1988, J. Immunol. 41:4224–4228; Lorberboum-Galski et al., 1990, J. Bio. Chem. 265:16311–16317).

A highly purified IL2-PE40 preparation (Bailon et al., 1988, Biotechnol. 6:1326–1329) was shown to (a) delay and mitigate adjuvant induced arthritis in rats (Case et al., 1989, Proc. Natl. Acad. Sci. U.S.A. 86:287–291), (b) significantly prolong the survival of vascularized heart allograft in mice (Lorberboum-Galski et al., 1989, Proc. Natl. Acad. Sci. U.S.A. 86:1008–1012) and corneal allografts in rats (Herbort et al., 1991, Transplant. 52:470–474), (c) reduce the incidence and severity of experimental autoimmune uveoretinitis in rats (Roberge et al., 1989, J. Immunol. 143:3498–3502), (d) suppress the growth of an IL2R bearing T cell lymphoma in mice (Kozak et al., 1990, J. Immunol. 145:2766–2771) and (e) prevent the development of experimental allergic encephalomyelitis, a T cell mediated disease of the central nervous system, in rats and mice (Beraud et al., 1991, Cell. Immunol. 133:379–389; Rose et al., 1991, J. Neuroimmunol. 32:209–217). However, such immunotoxin still suffers from the same deficiencies outlined above, particularly non-specific toxicity and immunogenicity in the human host.

2.2. APOPTOSIS-INDUCING PROTEINS

The development of multilineage organisms and the maintenance of homeostasis within tissues both require tightly regulated cell death. The ability of an individual cell to execute a suicidal response following a death stimulus varies markedly during its differentiation. Both positive and negative regulators of programmed cell death (apoptosis) have been identified.

A high percentage of follicular lymphomas have a characteristic chromosomal translocation, which places the proto-oncogene, Bcl-2 next to the immunoglobulin heavy chain locus, resulting in deregulation of Bcl-2 expression. Bcl-2 was found to function as a repressor of programmed cell death (Vaux et al., 1988, Nature 334:440–442). Recently, other Bcl-2 homologues were shown to inhibit apoptosis. However, one such homologue, Bax, mediates an opposite effect by accelerating apoptosis. An expanding family of Bcl-2 related proteins has recently been noted to share homology that is principally, but not exclusively, clustered within two conserved regions known as Bcl-2 homology domains 1 and 2 (BH1 and BH2) (Oltvai et al., 1993, Cell 74:609–619; Boise et al., 1993, Cell 74:597–608; Kozopas et al., 1993, Proc. Natl. Acad. Sci. U.S.A. 90:3516–3520; Lin et al., 1993, J. Immunol. 151:1979–1988). Members of the Bcl family include Bax, Bcl-$X_L$, Mcl-1, A1 and several open reading frames in DNA viruses. Another conserved domain in Bax, distinct from BH1 and BH2 was identified and termed BH3. This domain mediates cell death and protein binding functions (Chittenden et al., 1995, EMBO J. 14:5589–5596). Another member of the pro-apoptotic proteins contains only the BH3 domain, implying that this particular domain may be uniquely important in the promotion of apoptosis (Diaz et al., 1997, J. Biol. Chem. 272:11350–11355).

Bax homodimerizes and forms heterodimers with BCL-2 in vivo. Overexpressed Bax overcomes the death repressor activity of Bcl-2 (Oltvai et al., 1993, Cell 74:609–619). It was found that levels of Bax expression higher than Bcl-2 in bladder tumors was correlated with a better outcome for patients. Early relapses were much more frequently observed in patients whose tumors expressed more Bcl-2 than Bax mRNA (Gazzaniga et al., 1996, Int. J. Cancer 69:100–104).

Recently it was reported that Bax-alpha, a splice variant of Bax was expressed in high amount in normal breast epithelium, whereas only weak or no expression could be detected in 39 out of 40 cancer tissue samples examined (Bargou et al., 1996, J. Clin. Invest. 97:2651–2659). Of interest, downregulation of Bax-alpha was found in different histological subtypes. Furthermore, when Bax-alpha was transfected into breast cancer cell lines under the control of a tetracycline-dependent expression system, Bax restored sensitivity of the cancer cells toward both serum starvation and APO-I/Fas-triggered apoptosis, and significantly reduced tumor growth in SCID mice. Therefore, it was proposed that dysregulation of apoptosis might contribute to the pathogenesis of breast cancer at least in part due to an imbalance between members of the Bcl-2 gene family (Bargou et al., 1996, J. Clin. Invest. 97:2651–2659).

In another study, the expression of Bax was investigated in 52 cases of Hodgkin's disease in parallel with Epstein-Barr virus, and was compared with the immunodetection of other apoptosis-regulating proteins, Mcl-1, Bcl-2 and Bcl-x. Bax expression was frequently detected in Hodgkin's disease, providing an explanation for the good chemoresponses generally obtained for patients with this neoplastic disorder (Rigal-Haguet et al., 1996, Blood 87:2470–2475).

Additional members of this growing family of apoptosis inducing proteins have been cloned and identified. Bak is a new member of the Bcl-2 family which is expressed in a wide variety of cell types and binds to the Bcl-2 homologue Bcl-x2 in yeast (Farrow et al., 1995, Nature 374:731–733; Chittenden et al., 1995, Nature 374:733). A domain in Bak was identified as both necessary and sufficient for cytotoxicity activity and binding to Bcl-xl. Sequences similar to this domain that are distinct from BH1 and BH2 have been identified in Bax and Bip1. This domain was found to be of central importance in mediating the function of multiple cell death-regulatory proteins that interact with Bcl-2 family members (Chittenden et al., 1995, EMBO J. 14:5589–5596).

Overexpression of Bak in sympathetic neurons deprived of nerve growth factor accelerated apoptosis and blocked the protective effect of co-injected E1B 19K. The adenovirus E1B 19K protein is known to inhibit apoptosis induced by E1A, tumor-necrosis factor-alpha, FAS antigen and nerve growth factor deprivation (Farrow et al., 1995, Nature 374:731–733). Expression of Bak induced rapid and extensive apoptosis of serum-deprived fibroblasts, thus raising the possibility that Bak is directly involved in activating the cell death machinery (Chittenden et al., 1995, Nature 374:733–736). It was also reported that in the normal and neoplastic colon, mucosal expression of immunoreactive Bak co-localized with sites of epithelial cell apoptosis. Induction of apoptosis in the human colon cancer cell line HT29 and the rat normal small intestinal cell line 1EC 18 in culture was accompanied by increased Bak expression without consistent changes in expression of other Bcl-2 homologous proteins (Moss et al., 1996, Biochem. Biophys. Res. Commun. 223:199–203). Therefore, Bak was also suggested to be the endogenous Bcl-2 family member best correlated with intestinal cell apoptosis (Moss et al., 1996, Biochem. Biophys. Res. Commun. 223:119–203).

Unlike Bax, however, Bak can inhibit cell death in an Epstein-Barr-virus-transformed cell line. Tissues with unique distribution of Bak messenger RNA include those containing long-lived, terminally differentiated cell types (Krajewski et al., 1996, Cancer Res. 56:2849–2855), suggesting that cell-death-inducing activity is broadly distributed, and that tissue-specific modulation of apoptosis is controlled primarily by regulation of molecules that inhibit apoptosis (Kiefer et al., 1995, Nature 374:736–739).

Another member of the Bcl2 family is Bad that possesses the key amino acid motifs of BH1 and BH2 domains. Bad lacks the classical C-terminal signal-anchor sequence responsible for the integral membrane positions of other family members. Bad selectively dimerizes with Bcl-$x_L$ as well as Bcl-2, but not with Bax, Bcl-Xs-Mcl1, A1 or itself. Bad reverses the death repressor activity of Bcl-$X_L$, but not that of Bcl-2 (Yang et al., 1995, Cell 80:285–291; Ottilie et al., 1997, J. Biol. Chem. 272:30866–30872; Zha et al., 1997, J. Biol. Chem. 272:24101–24104).

Another member is Bik which interacts with the cellular survival-promoting proteins, Bcl-2 and Bcl-$X_L$ as well as the viral survival-promoting proteins, Epstein Barr virus-BHRF1 and adenovirus E1B-19 kDa. In transient transfection assays, Bik promotes cell death in a manner similar to other death-promoting members of the Bcl-2 family, Bax and Bak. This death-promoting activity of Bik can be suppressed by coexpression of Bcl-2, Bcl-$X_L$, EBV-BHRF1 and E1B-19 kDa proteins suggesting that Bik may be a common target for both cellular and viral anti-apoptotic proteins. While Bik does not contain overt homology to the BH1 and BH2 conserved domains characteristic of the Bcl-2 family, it shares a 9 amino acid domain (BH3) with Bax and Bak which may be a critical determinant for the death-promoting activity of these proteins (Boyd et al., 1995, Oncogene 11:1921–1928; Han et al., 1996, Mol. Cell. Biol. 16:5857–5864).

The Bcl-2 family is composed of various pairs of antagonist and agonist proteins that regulate apoptosis. Whether their function is interdependent is uncertain. Using a genetic approach to address this question, Knudson et al. (1997, Nature Genetics 16:358–363), recently utilized gain—and loss of—function models of Bcl-2 and Bax, and found that apoptosis and thymic hypoplasia, characteristic of Bcl-2-deficient mice, are largely absent in mice also deficient in Bax. A single copy of Bax promoted apoptosis in the absence of Bcl-2. In contrast, overexpression Bcl-2 still repressed apoptosis in the absence of Bax. While an in vivo competition exists between Bax and Bcl-2, each is able to regulate apoptosis independently. Bax has been shown to form channels in lipid membranes and trigger the release of liposome-encapsulated carboxyluorescein at both neutral and acidic pH. At physiological pH, release could be blocked by Bcl-2. In planer lipid bilayers, Bax formed pH- and voltage-dependent ion-conduction channels. Thus, the pro-apoptotic effects of Bax may be elicited through an intrinsic pore-forming activity that can be antagonized by Bcl-2 (Antonsson et al., 1997, Science 277:370–372). Two other members of this family, Bcl-2 and Bcl-1, were also shown to form pores in lipid membranes (Schendel et al., 1997, Proc. Natl. Acad. Sci. U.S.A. 94:5113–5118).

Prior to the present invention, a fusion protein containing a Bcl-2 pro-apoptotic member was not reported, nor was it predictable if such a molecule could retain biological activites when added to a cell exogenously to induce apoptosis.

3. SUMMARY OF THE INVENTION

The present invention relates to chimeric proteins with cell-targeting specificity and apoptosis-inducing activities. The chimeric proteins of the invention are composed of a cell-specific targeting moiety and an apoptosis-inducing moiety. The cell-specific targeting moiety provides cell-specific binding properties to the chimeric protein, while the apoptosis-inducing moiety induces programmed cell death upon entry into a target cell. It is preferred that the chimeric proteins of the invention be produced by recombinant expression of a fusion polynucleotide between a coding sequence of a cell-targeting moiety and a coding sequence of an apoptosis-inducing protein. Such chimeric proteins are likely to be superior to the immunotoxins currently used in the art because they are of human origin and thus are expected to have reduced immunogenicity in a human recipient. In addition, chimeric proteins kill target cells by inducing apoptosis which does not cause a release of cellular organelles into the extracellular environment to result in an inflammatory response. When cells die by the apoptotic pathway, they shrink and condense, but the organelles and plasma membranes retain their integrity, and the dead cells are rapidly phagocytosed by neighboring cells or macrophages before there is leakage of the cells' contents, thereby eliciting minimal tissue or systemic response.

The invention also relates to pharmaceutical compositions of the chimeric proteins, methods of producing such proteins, and methods of using the same in vitro and in vivo, especially for eliminating specific undesirable target cells, and for the treatment of a variety of disease conditions as well as the use of the proteins for disease diagnosis.

The invention is based, in part, on the Applicants' discovery that a partially purified recombinant chimeric protein, IL2-Bax, specifically targets $IL2R^+$ cells, which include but are not limited to, T. cells, B cells, monocytes and natural killer cells. The protein kills target cells by inducing apoptosis of these cells. A wide variety of uses are encompassed by the present invention, including but not limited to, the treatment of autoimmunity, transplantation rejection, graft-versus-host disease, cancer, hypersensitivity, and infectious diseases.

4. BRIEF DESCRIPTION OF THE DRAWINGS

FIG. 1: Construction of the pSY1 plasmid that encodes a chimeric protein composed of IL2 and Bax-α (designated IL2-Bax) under the control of the T7 promoter SEQ ID NOS: 9 and 10. The numbers represent the corresponding amino acids.

FIG. 2: Nucleotide sequence (SEQ ID NO:1) of a coding sequence for chimeric protein, IL2-Bax, and its deduced amino acid sequence (SEQ ID NO:2).

Figure 3:
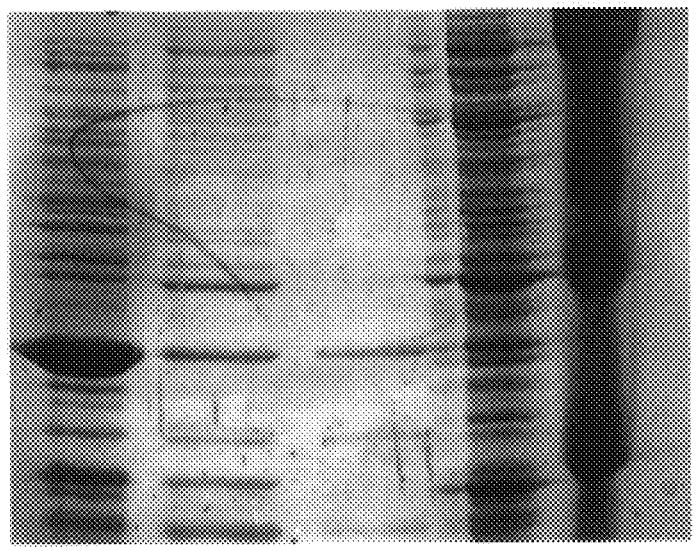

FIG. 3: SDS-PAGE analysis of cell fractions containing the IL2-Bax chimeric protein. IL2-Bax was overexpressed in *E. coli* BL21 (λDE3) and subfractionated as described in Section 6.1.2., infra. Samples of each subfraction were mixed with Laemmli sample buffer and loaded on a 10% polyacrylamide gel. Lanes: 1, insoluble fraction treated with extraction buffer B containing SDS. 2, insoluble fraction treated with extraction buffer C containing urea. 3, insoluble fraction treated with extraction buffer A, containing Gu-HCL. 4, soluble fraction. M, markers. Arrow indicates the position of the IL2-Bax chimeric protein.

Figure 4:
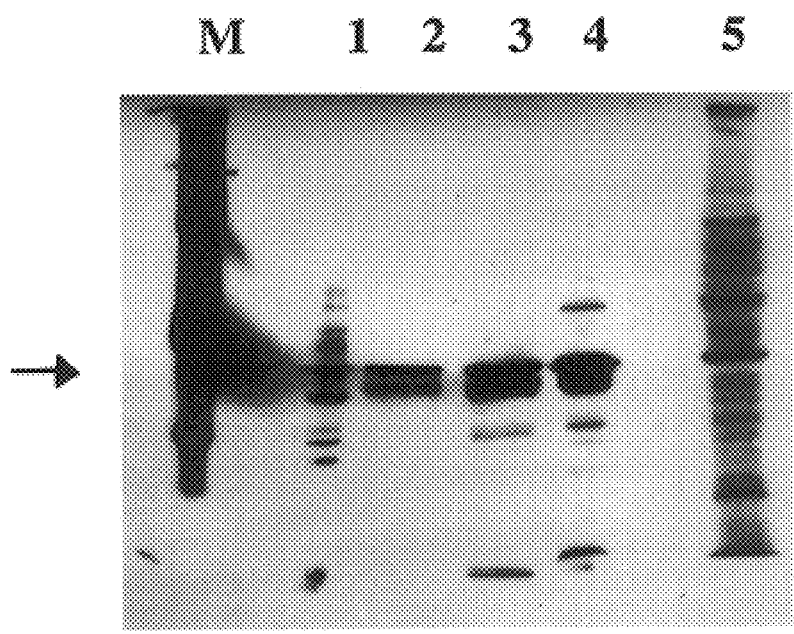

FIG. 4: Immunobloting of fractions containing IL2-Bax with antibodies to the Bax protein. Lanes: 1, soluble fraction. 2, insoluble fraction treated with extraction buffer A containing Gu-HCL. 3, insoluble fraction treated with extraction buffer C containing urea. 4, insoluble fraction treated with extraction buffer B containing SDS. 5, A protein extract of MCF-7 cells known to express the Bax protein (indicated by the *). Arrow indicates the position of the IL2-Bax chimeric protein.

Figure 5A:
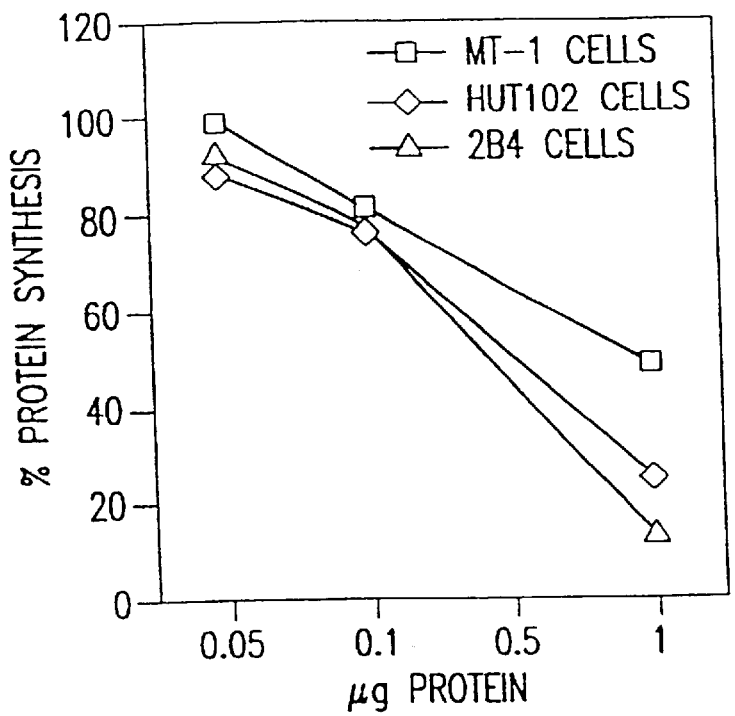

FIGS. 5A&B: Effect of IL2-Bax on protein synthesis in target (5A) and non-target (5B) cell lines. IL2-Bax (insoluble fraction treated with Gu-HCL) was added at different concentrations to the various cell lines. [$^3$H] leucine incorporation into cellular protein was measured. Results are expressed as percent of control cells not exposed to IL2-Bax.

FIGS. 6A–D: FACS analysis of fresh lymphocytes exposed to IL2-Bax. Fresh lymphocytes were separated, exposed to the IL2-Bax chimeric protein and apoptotic cells were analyzed by FACS. The cells were untreated (6A) or treated with dexamethasone (6B), IL2-Bax at 1 μg/ml (6C) or IL2-Bax at 10 μg/ml (6D).

Figure 7A:
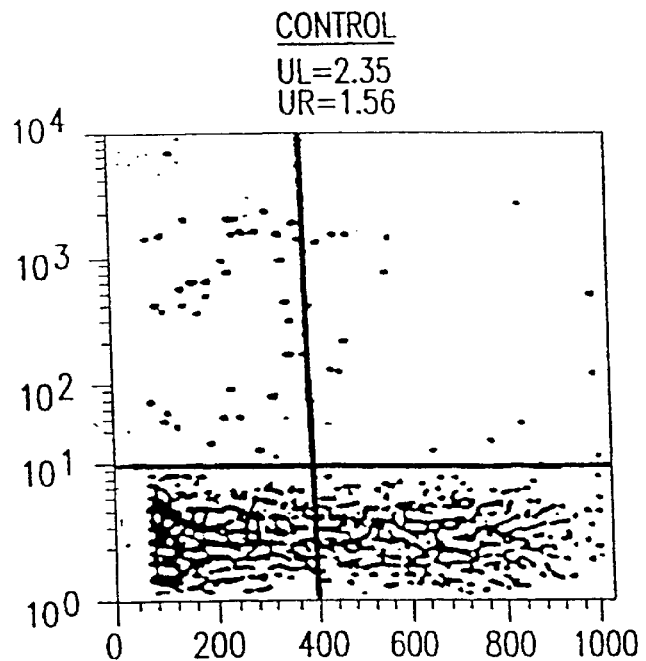
Figure 7B:
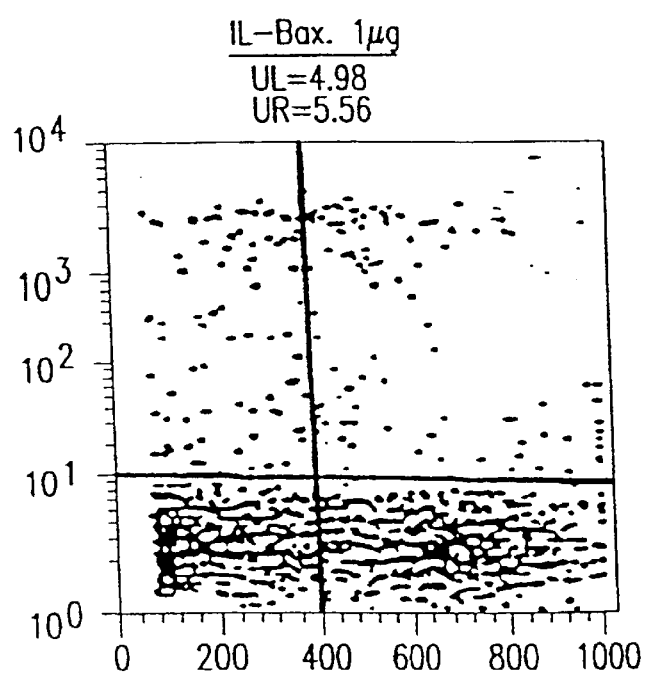
Figure 7C:
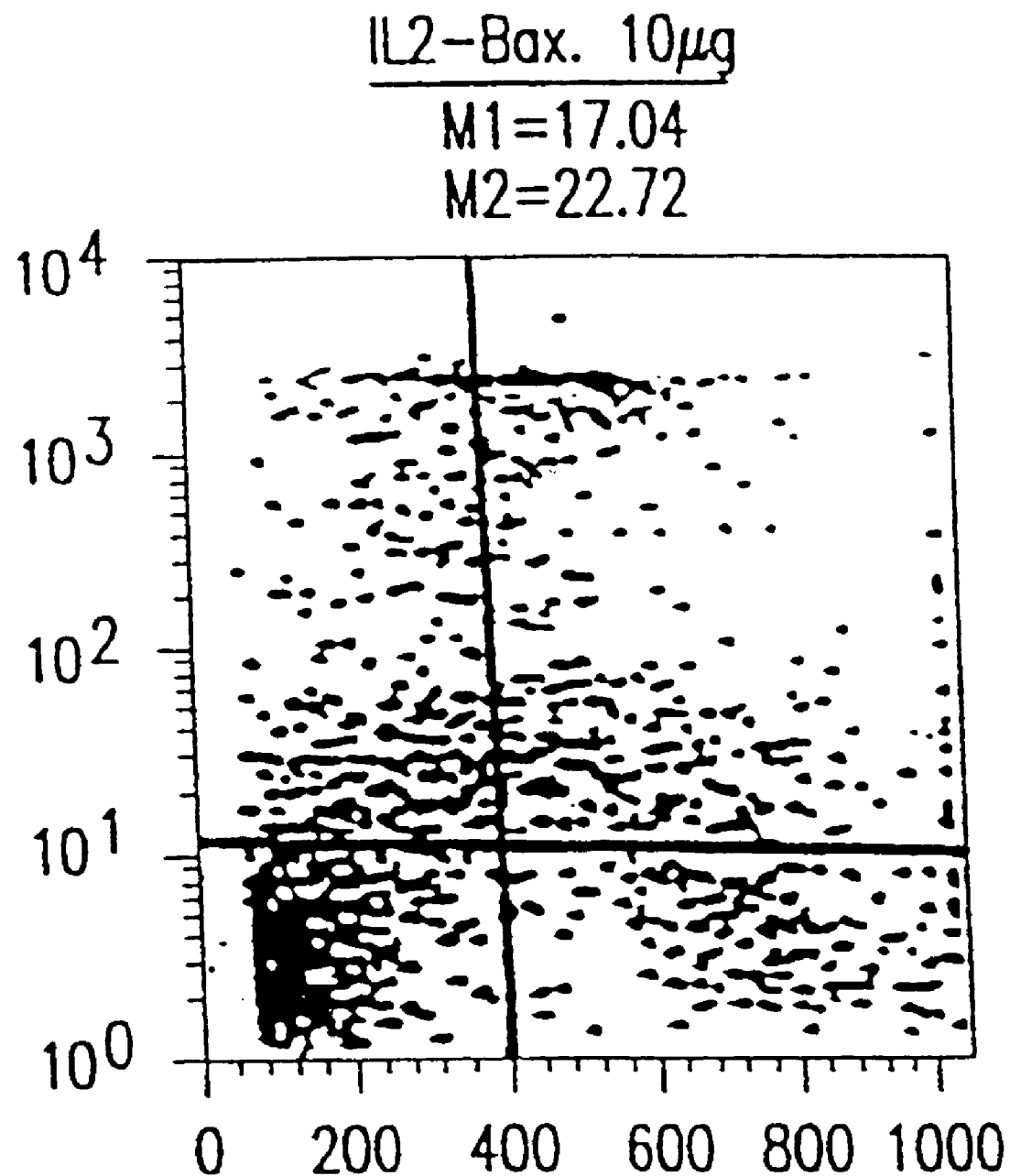
Figure 8B:
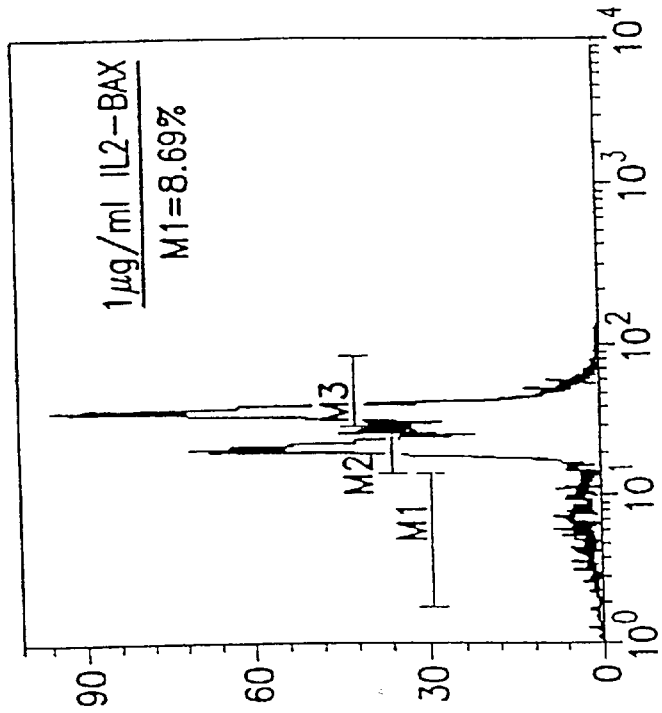
Figure 8A:
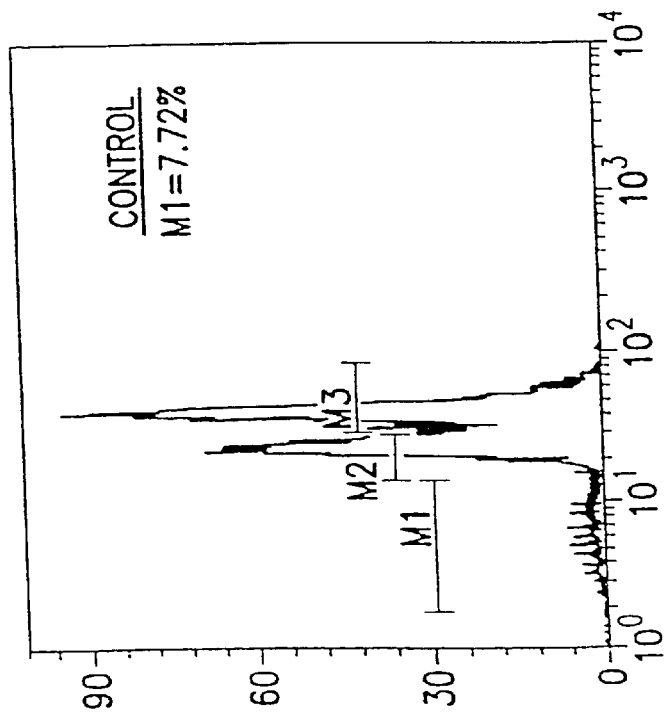
Figure 8D:
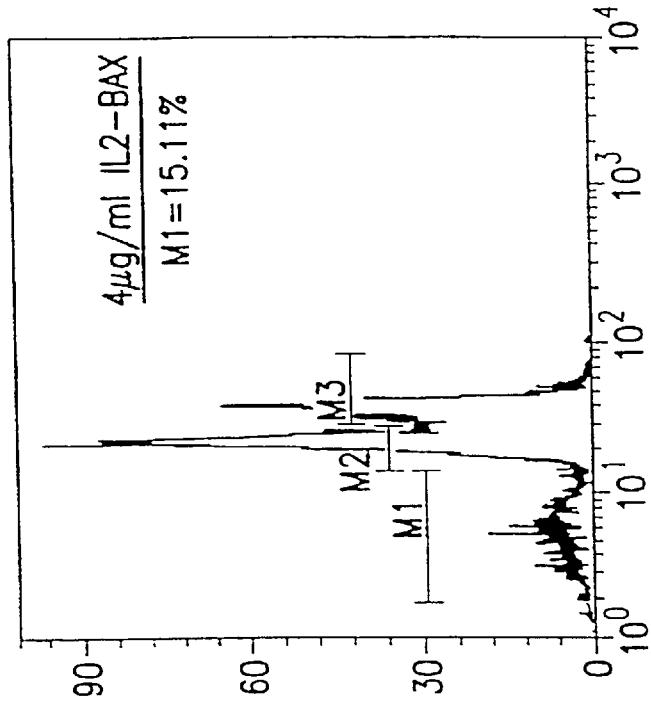
Figure 8C:
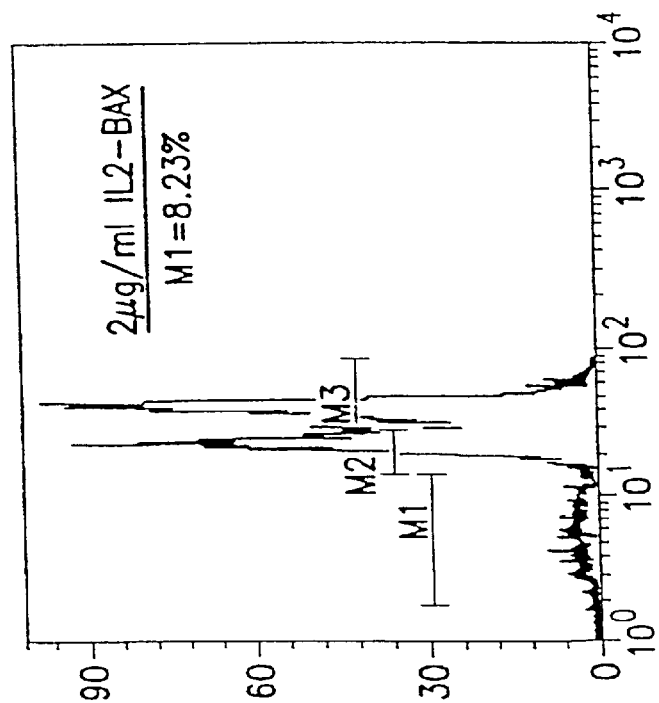
Figure 8E:
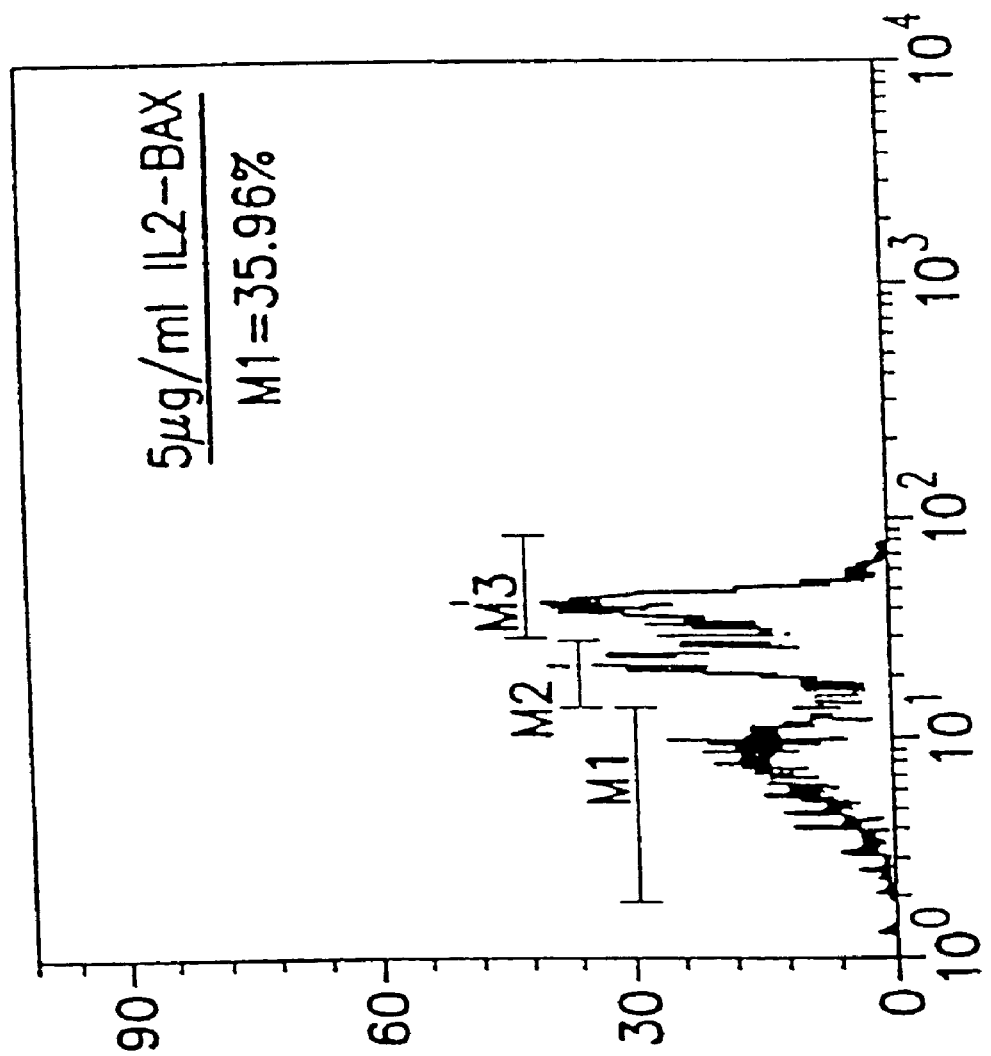

FIGS. 7A–C: FACS analysis of fresh lymphocytes exposed to IL2-Bax. Fresh lymphocytes were separated, exposed to the IL2-Bax chimeric protein and apoptotic cells were analyzed by FACS. The cells were untreated (7A) or treated with IL2-Bax at 1 μg/ml (7B) or IL2-Bax at 10 μg/ml (7C).

FIGS. 8A–E: FACS analysis of HUT102 exposed to IL2-Bax. HUT102 cells were exposed to IL2-Bax chimeric protein and analyzed by FACS to characterize apoptotic cells. Results are expressed in a logarithmic mode. The cells were untreated (8A) or treated with IL2-Bax at 1 μg/ml (8B), IL2-Bax at 2 μg/ml (8C), IL2-Bax at 4 μg/ml (8D) or IL2-Bax at 5 μg/ml (8E).

Figure 9A:
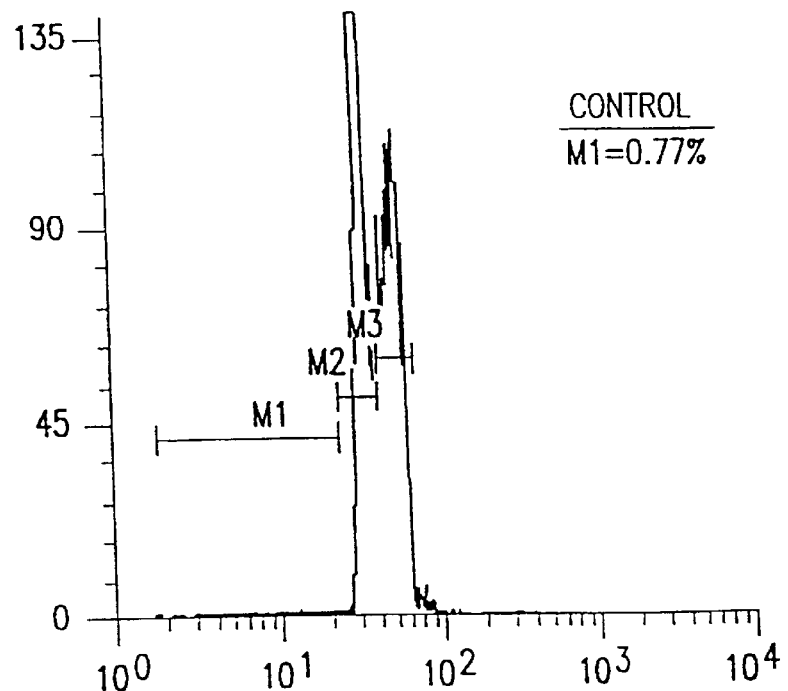
Figure 9B:
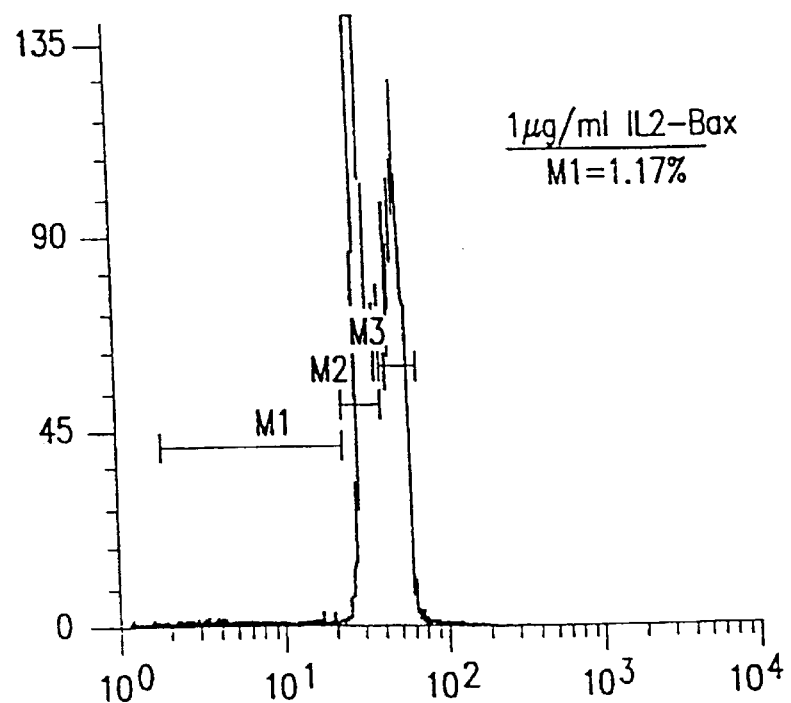
Figure 9C:
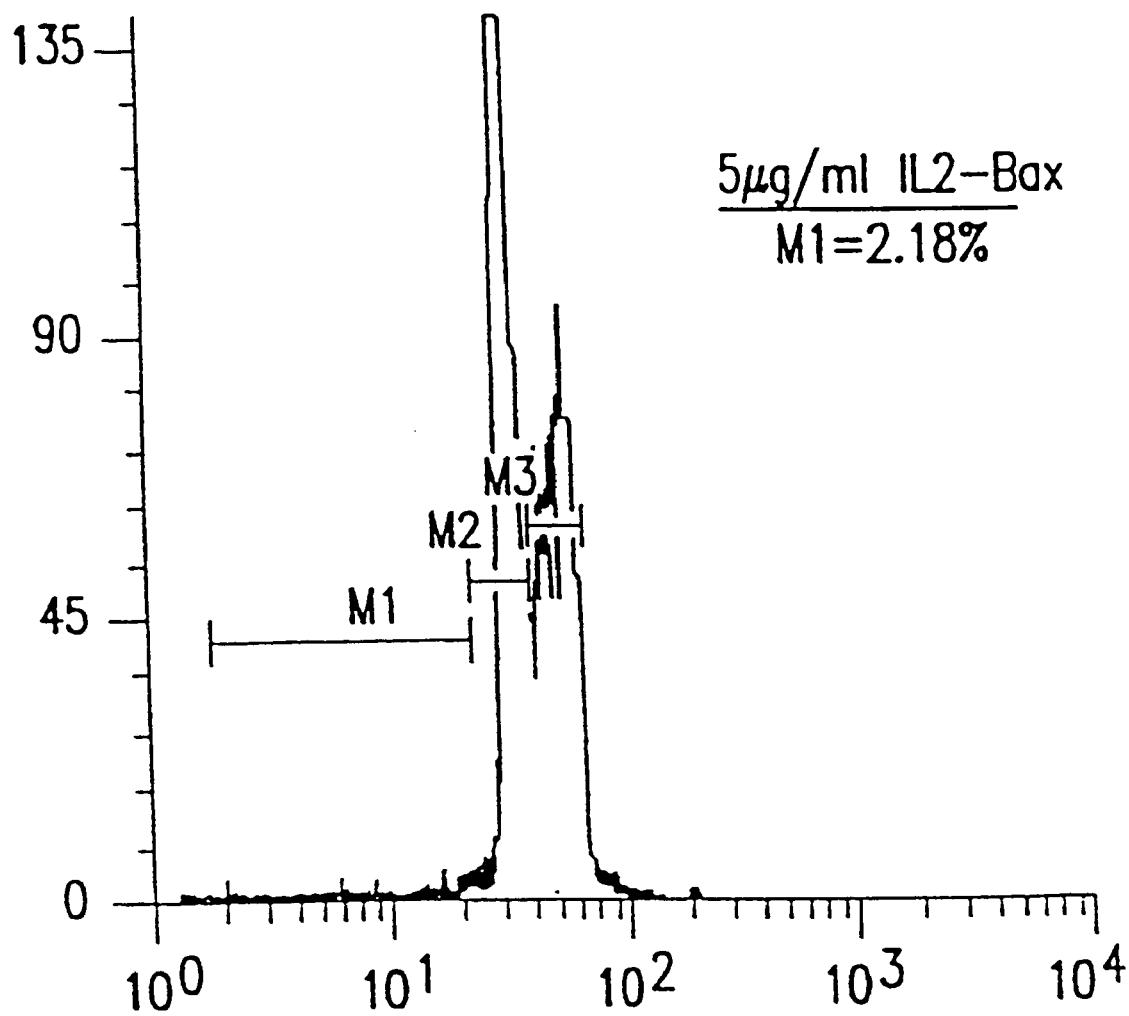

FIGS. 9A–C: FACS analysis of CEM cells exposed to IL2-Bax. CEM cells were exposed to IL2-Bax chimeric protein and analyzed by FACS to characterize apoptotic cells. Results are expressed in a logarithmic mode. The cells were untreated (9A) or treated with IL2-Bax at 1 μg/ml (9B) or IL2-Bax at 5 μg/ml (9C).

5. DETAILED DESCRIPTION OF THE INVENTION

The present invention relates to chimeric proteins, pharmaceutical compositions of chimeric proteins, methods of producing a chimeric protein and methods of using the protein. For clarity of discussion, the specific compositions, procedures and methods described herein are exemplified using IL2 and Bax; they are merely illustrative for the practice of the invention. Analogous procedures and techniques are equally applicable to constructing other chimeric proteins between any cell-specific targeting moiety and apoptosis-inducing moiety.

5.1. CONSTRUCTION OF CHIMERIC MOLECULES

While the chimeric proteins of the present invention may be produced by chemical synthetic methods or by chemical linkage between the two moieties, it is preferred that they are produced by fusion of a coding sequence of a cell-specific targeting moiety and a coding sequence of an apoptosis-inducing protein under the control of a regulatory sequence which directs the expression of the fusion polynucleotide in an appropriate host cell. The fusion of two full length coding sequences can be achieved by methods well known in the art of molecular biology. It is preferred that a fusion polynucleotide contain only the AUG translation initiation codon at the 5' end of the first coding sequence without the initiation codon of the second coding sequence to avoid the production of two encoded product. In addition, a leader sequence may be placed at the 5' end of the polynucleotide in order to target the expressed product to a specific site or compartment within a host cell to facilitate secretion or subsequent purification after gene expression. The two coding sequences can be fused directly without any linker or by using a flexible polylinker composed of the pentamer Gly-Gly-Gly-Gly-Ser (SEQ ID NO:5) repeated 1 to 3 times. Such linker has been used in constructing single chain antibodies (scFv) by being inserted between $V_H$ and $V_L$ (Bird et al., 1988, Science 242:423–426; Huston et al., 1988, Proc. Natl. Acad. Sci. U.S.A. 85:5979–5883). The linker is designed to enable the correct interaction between two beta-sheets forming the variable region of the single chain antibody. Other linkers which may be used include Glu-Gly-Lys-Ser-Ser-Gly-Ser-Gly-Ser-Glu-Ser-Lys-Val-Asp (SEQ ID NO: 6) (Chaudhary et al., 1990, Proc. Natl. Acad. Sci. U.S.A. 87:1066–1070) and Lys-Glu-Ser-Gly-Ser-Val-Ser-Ser-Glu-Gln-Leu-Ala-Gln-Phe-Arg-Ser-Leu-Asp (SEQ ID NO: 7) (Bird et al., 1988, Science 242:423–426).

5.1.1. CELL-SPECIFIC TARGETING MOIETIES

The chimeric proteins of the invention are composed of a cell-specific targeting moiety and an apoptosis-inducing moiety. The cell-specific targeting moiety confers cell-type specific binding to the molecule, and it is chosen on the basis of the particular cell population to be targeted. A wide variety of proteins are suitable for use as cell-specific targeting moieties, including but not limited to, ligands for receptors such as growth factors, hormones and cytokines, and antibodies or antigen-binding fragments thereof.

Since a large number of cell surface receptors have been identified in hematopoietic cells of various lineages, ligands or antibodies specific for these receptors may be used as cell-specific targeting moieties. In a specific embodiment illustrated by working examples in Section 6, infra, IL2 was used as the cell-specific targeting moiety in a chimeric protein to target IL2R$^+$ cells. In addition, other molecules such as B7–1, B7–2 and CD40 may be used to specifically target activated T cells (The Leucocyte Antigen Facts Book, 1993, Barclay et al. (eds.), Academic Press). On the other hand, B cells express CD19, CD40 and IL4 receptor and may be targeted by moieties that bind these receptors. Examples of such moieties include CD40 ligand, IL4, IL5, IL6 and CD28. The elimination of immune cells such as T cells and B cells is particularly useful in the treatment of autoimmunity, hypersensitivity, transplantation rejection responses and in the treatment of lymphoid tumors. Examples of autoimmune diseases are multiple sclerosis, rheumatoid arthritis, insulin-dependent diabetes mellitus, systemic lupus erythematosis, scleroderma, uviatis, and the like. More specifically, since myelin basic protein is known to be the major target of immune cell attack in multiple sclerosis, this protein may be used as a cell-specific targeting moiety for the treatment of multiple sclerosis (WO 97/19179; Becker et al., 1997, Proc. Natl. Acad. Sci. U.S.A. 94:10873).

Other cytokines which may be used to target specific cell subsets include the interleukins (IL1-IL15), granulocyte-colony stimulating factor, macrophage-colony stimulating factor, granulocyte-macrophage colony stimulating factor, leukemia inhibitory factor, tumor necrosis factor, transforming growth factor, epidermal growth factor, insulin-like growth factors, fibroblast growth factor and the like (Thompson (ed.), 1994, The Cytokine Handbook, Academic Press, San Diego).

Additionally, certain cell surface molecules are highly expressed in tumor cells, including hormone receptors such as human chorionic gonadotropin receptor and gonadotropin releasing hormone receptor (Nechushtan et al., 1997, J. Biol. Chem. 272:11597). Therefore, the corresponding hormones may be used as the cell-specific targeting moieties in cancer therapy.

Antibodies are the most versatile cell-specific targeting moieties because they can be generated against any cell surface antigen of interest. Monoclonal antibodies have been generated against cell surface receptors, tumor-associated antigens, and leukocyte lineage-specific markers such as CD antigens. Antibody variable region genes can be readily isolated from hybridoma cells by methods well known in the art. However, since antibodies are assembled between two heavy chains and two light chains, it is preferred that a scFv be used as a cell-specific targeting moiety in the present invention. Such scFv are comprised of $V_H$ and $V_L$ domains linked into a single polypeptide chain by a flexible linker peptide. Furthermore, the Fc portion of the heavy chain of an antibody may be used to target Fc receptor-expressing cells such as the use of the Fc portion of an IgE antibody to target mast cells and basophils. The specific targeting of these cell types is useful for treating IgE-mediated hypersensitivity in humans and animals (Helm et al., 1988, Nature 331:180–183; PCT/IL96/00181).

5.1.2. APOPTOSIS-INDUCING MOIETIES

The pro-apoptotic proteins in the BCL2 family are particularly suitable for use as the apoptosis-inducing moieties in the present invention. Such human proteins are expected to have reduced immunogenicity over many immunotoxins composed of bacterial toxins. In a specific embodiment illustrated by working examples in Section 6, infra, the bax coding sequence is fused with an IL2 coding sequence for the production of a chimeric protein IL2-Bax. While Bax is the preferred apoptosis-inducing moiety, other members in this family suitable for use in the present invention include Bak (Farrow et al., 1995, Nature 374:731; Chittenden et al., 1995, Nature 374:733; Kiefer et al., 1995, Nature 374:736), Bcl-$X_s$ (Boise et al., 1993, Cell 74:597; Fang et al., 1994, J.Immunol. 153:4388), Bad (Yang et al., 1995, Cell 80:285), Bid (Wang et al., 1996, Genes Develop. 10:2859–2869), Bik (Bovd et al., 1995, Oncogene 11:1921–1928), Hrk (Inohara et al., 1997, EMBO J. 16:1686–1694) and Bok (Hsu et al., 1997, Proc. Natl. Acad. Sci. USA 94: 12401–12406). The nucleotide sequences encoding these proteins are known in the art, and thus cDNA clones can be readily obtained for fusion with a coding sequence for a cell-specific targeting moiety in an expression vector.

Specific domains of certain of the Bcl-2 family members have been studied with respect to their apoptosis-inducing activities. For example, the GD domain of Bak is involved in the apoptosis function (U.S. Pat. No. 5,656,725). In addition, Bax and Bip1a are shown to share a homologous domain. Therefore, any biologically active domains of the Bcl-2 family may be used as an apoptosis-inducing moiety for the practice of the present invention.

Caspases also play a central role in apoptosis and may well constitute part of the consensus core mechanism of apoptosis. Caspases are implicated as mediators of apoptosis. Since the recognition that CED-3, a protein required for developmental cell death, has sequence identity with the mammalian cysteine protease interleukin-1 beta-converting enzyme (ICE), a family of at least 10 related cysteine proteases has been identified. These proteins are characterized by almost absolute specificity for aspartic acid in the P1 position. All the caspases (ICE-like proteases) contain a conserved QACXG (SEQ ID NO: 8 (where X is R, Z or G) pentapeptide active-site motif. Caspases are synthesized as inactive proenzymes comprising an N-terminal peptide (Prodomain) together with one large and one small subunit. The crystal structures of both caspase-1 and caspase-3 show that the active enzyme is a heterotetramer, containing two small and two large subunits. Activation of caspases during apoptosis results in the cleavage of critical cellular substrates, including poly(ADP-ribose) polymerase and lamins, so precipitating the dramatic morphological changes of apoptosis (Cohen, 1997, Biochem. J. 326:1–16). Therefore, it is also within the scope of the present invention to use a caspase as an apoptosis-inducing moiety.

Recently a few new proteins were cloned and identified as factors required for mediating activity of proteins, mainly caspases, involved in the apoptosis pathway. One factor was identified as the previously known electron transfer protein, cytochrome c (Lin et al., 1996, Cell 86:147–157), designed as Apaf-2. In addition to cytochrome c the activation of caspase-3 requires two other cytosolic factors-Apaf-1 and Apaf-3. Apaf-1 is a protein homologous to C. elegans CED-4, and Apaf-3 was identified as a member of the caspase family, caspase-9. Both factors bind to each other via their respective NH2-terminal CED-3 homologous domains, in the presence of cytochrome c, an event that leads to caspase-9 activation. Activated caspase-9 in turn cleaves and activates caspase-3 (Liu et al., 1996, Cell 86:147–157; Zou et al., 1997, Cell 90:405–413; Li et al., 1997, Cell 91:479–489). Another protein involved in the apoptotic pathway is DNA fragmentation factor (DFF), a heterodimer of 45 and 40 kd subunits that functions downstream of caspase-3 to trigger fragmentation of genomic DNA into nucleosomal segments (Liu et al., 1997, Cell 89:175–184).

5.2. EXPRESSION OF CHIMERIC PROTEINS

In accordance with the invention, a polynucleotide which encodes a chimeric protein, mutant polypeptides, biologically active fragments of chimeric protein, or functional equivalents thereof, may be used to generate recombinant DNA molecules that direct the expression of the chimeric protein, chimeric peptide fragments, or a functional equivalent thereof, in appropriate host cells.

Due to the inherent degeneracy of the genetic code, other DNA sequences which encode substantially the same or a functionally equivalent amino acid sequence, may be used in the practice of the invention for the cloning and expression of the chimeric protein. Such DNA sequences include those which are capable of hybridizing to the chimeric sequences or their complementary sequences under stringent conditions. The phrase "stringent conditions" as used herein refers to those hybridizing conditions that (1) employ low ionic strength and high temperature for washing, for example, 0.015 M NaCl/0.0015 M sodium citrate/0.1% SDS at 50° C.; (2) employ during hybridization a denaturing agent such as formamide, for example, 50% (vol/vol) formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C.; or (3) employ 50% formamide, 5×SSC (0.75 M NaCl, 0.075 M Sodium pyrophosphate, 5×Denhardt's solution, sonicated salmon sperm DNA (50 μg/ml), 0.1% SDS, and 10% dextran sulfate at 42° C., with washes at 42° C. in 0.2×SSC and 0.1% SDS.

Altered DNA sequences which may be used in accordance with the invention include deletions, additions or substitutions of different nucleotide residues resulting in a sequence that encodes the same or a functionally equivalent fusion gene product. The gene product itself may contain deletions, additions or substitutions of amino acid residues within a chimeric sequence, which result in a silent change thus producing a functionally equivalent chimeric protein. Such amino acid substitutions may be made on the basis of similarity in polarity, charge, solubility, hydrophobicity, hydrophilicity, and/or the amphipathic nature of the residues involved. For example, negatively charged amino acids include aspartic acid and glutamic acid; positively charged amino acids include lysine, histidine and arginine; amino acids with uncharged polar head groups having similar hydrophilicity values include the following: glycine, asparagine, glutamine, serine, threonine, tyrosine; and amino acids with nonpolar head groups include alanine, valine, isoleucine, leucine, phenylalanine, proline, methionine, tryptophan.

The DNA sequences of the invention may be engineered in order to alter a chimeric coding sequence for a variety of ends, including but not limited to, alterations which modify processing and expression of the gene product. For example, mutations may be introduced using techniques which are well known in the art, e.g., site-directed mutagenesis, to insert new restriction sites, to alter glycosylation patterns, phosphorylation, etc.

In an alternate embodiment of the invention, the coding sequence of the chimeric protein could be synthesized in whole or in part, using chemical methods well known in the art. See, for example, Caruthers et al., 1980, *Nuc. Acids Res. Symp. Ser.* 7:215–233; Crea and Horn, 180, *Nuc. Acids Res.* 9(10):2331; Matteucci and Caruthers, 1980, *Tetrahedron Letter* 21:719; and Chow and Kempe, 1981, *Nuc. Acids Res.* 9(12):2807–2817. For example, active domains of the moieties can be synthesized by solid phase techniques, cleaved from the resin, and purified by preparative high performance liquid chromatography followed by chemical linkage to form a chimeric protein. (e.g., see Creighton, 1983, *Proteins Structures And Molecular Principles,* W. H. Freeman and Co., N.Y. pp. 50–60). The composition of the synthetic peptides may be confirmed by amino acid analysis or sequencing (e.g., the Edman degradation procedure; see Creighton, 1983, *Proteins, Structures and Molecular Principles*, W. H. Freeman and Co., N.Y., pp. 34–49). Alternatively, the two moieties of the chimeric protein produced by synthetic or recombinant methods may be conjugated by chemical linkers according to methods well known in the art (Brinkmann and Pastan, 1994, *Biochemica et Biophysica Acta* 1198:27–45).

In order to express a biologically active chimeric protein, the nucleotide sequence coding for a chimeric protein, or a functional equivalent, is inserted into an appropriate expression vector, i.e., a vector which contains the necessary elements for the transcription and translation of the inserted coding sequence. The chimeric gene products as well as host cells or cell lines transfected or transformed with recombinant chimeric expression vectors can be used for a variety of purposes. These include but are not limited to generating antibodies (i.e., monoclonal or polyclonal) that bind to epitopes of the proteins to facilitate their purification.

Methods which are well known to those skilled in the art can be used to construct expression vectors containing the chimeric protein coding sequence and appropriate transcriptional/translational control signals. These methods include in vitro recombinant DNA techniques, synthetic techniques and in vivo recombination/genetic recombination. See, for example, the techniques described in Sambrook et al., 1989, Molecular Cloning A Laboratory Manual, Cold Spring Harbor Laboratory, N.Y. and Ausubel et al., 1989, Current Protocols in Molecular Biology, Greene Publishing Associates and Wiley Interscience, N.Y.

A variety of host-expression vector systems may be utilized to express the chimeric protein coding sequence. These include but are not limited to microorganisms such as bacteria transformed with recombinant bacteriophage DNA, plasmid DNA or cosmid DNA expression vectors containing the chimeric protein coding sequence; yeast transformed with recombinant yeast expression vectors containing the chimeric protein coding sequence; insect cell systems infected with recombinant virus expression vectors (e.g., baculovirus) containing the chimeric protein coding sequence; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing the chimeric protein coding sequence; or animal cell systems. It should be noted that since most apoptosis-inducing proteins cause programmed cell death in mammalian cells, it is preferred that the chimeric protein of the invention be expressed in prokaryotic or lower eukaryotic cells. Section 6 illustrates that IL2-Bax may be efficiently expressed in *E. coli*.

The expression elements of each system vary in their strength and specificities. Depending on the host/vector system utilized, any of a number of suitable transcription and translation elements, including constitutive and inducible promoters, may be used in the expression vector. For example, when cloning in bacterial systems, inducible promoters such as pL of bacteriophage λ, plac, ptrp, ptac (ptrp-lac hybrid promoter; cytomegalovirus promoter) and the like may be used; when cloning in insect cell systems, promoters such as the baculovirus polyhedrin promoter may be used; when cloning in plant cell systems, promoters derived from the genome of plant cells (e.g., heat shock promoters; the promoter for the small subunit of RUBISCO; the promoter for the chlorophyll α/β binding protein) or from plant viruses (e.g., the 35S RNA promoter of CaMV; the coat protein promoter of TMV) may be used; when cloning in mammalian cell systems, promoters derived from the genome of mammalian cells (e.g., metallothionein promoter) or from mammalian viruses (e.g., the adenovirus late promoter; the vaccinia virus 7.5K promoter) may be used; when generating cell lines that contain multiple copies of the chimeric DNA, SV40-, BPV- and EBV-based vectors may be used with an appropriate selectable marker.

In bacterial systems a number of expression vectors may be advantageously selected depending upon the use intended for the chimeric protein expressed. For example, when large quantities of chimeric protein are to be produced, vectors which direct the expression of high levels of protein products that are readily purified may be desirable. Such vectors include but are not limited to the pHL906 vector (Fishman et al., 1994, Biochem. 33:6235–6243), the *E. coli* expression vector pUR278 (Ruther et al., 1983, EMBO J. 2:1791), in which the chimeric protein coding sequence may be ligated into the vector in frame with the lacZ coding region so that a hybrid AS-lacZ protein is produced; pIN vectors (Inouye & Inouye, 1985, Nucleic acids Res. 13:3101–3109; Van Heeke & Schuster, 1989, J. Biol. Chem. 264:5503–5509); and the like.

An alternative expression system which could be used to express chimeric protein is an insect system. In one such system, *Autographa californica* nuclear polyhidrosis virus (AcNPV) is used as a vector to express foreign genes. The virus grows in *Spodoptera frugiperda* cells. The chimeric protein coding sequence may be cloned into non-essential regions (for example the polyhedrin gene) of the virus and placed under control of an AcNPV promoter (for example the polyhedrin promoter). Successful insertion of the chimeric protein coding sequence will result in inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed. (e.g., see Smith et al., 1983, J. Viol. 46:584; Smith, U.S. Pat. No. 4,215,051).

Specific initiation signals may also be required for efficient translation of the inserted chimeric protein coding sequence. These signals include the ATG initiation codon and adjacent sequences. In cases where the entire chimeric gene, including its own initiation codon and adjacent sequences, is inserted into the appropriate expression vector, no additional translational control signals may be needed. However, in cases where the chimeric protein coding sequence does not include its own initiation codon, exogenous translational control signals, including the ATG initiation codon, must be provided. Furthermore, the initiation codon must be in phase with the reading frame of the chimeric protein coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., 1987, Methods in Enzymol. 153:516–544).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. The presence of consensus N-glycosylation sites in a chimeric protein may require proper modification for optimal chimeric protein function. Different host cells have characteristic and specific mechanisms for the post-translational processing and modification of proteins. Appropriate cell lines or host systems can be chosen to ensure the correct modification and processing of the chimeric protein. To this end, eukaryotic host cells which possess the cellular machinery for proper processing of the primary transcript, glycosylation, and phosphorylation of the chimeric protein may be used. Such mammalian host cells include but are not limited to CHO, VERO, BHK, HeLa, COS, MDCK, 293, WI38, and the like.

For long-term, high-yield production of recombinant chimeric proteins, stable expression is preferred. For example, cell lines which stably express the chimeric protein may be engineered. Rather than using expression vectors which contain viral origins of replication, host cells can be transformed with a chimeric coding sequence controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including but not limited to the herpes simplex virus thymidine kinase (Wigler et al., 1977, Cell 11:223), hypoxanthine-guanine phosphoribosyltransferase (Szybalska & Szybalski, 1962, Proc. Natl. Acad. Sci. USA 48:2026), and adenine phosphoribosyltransferase (Lowy et al., 1980, Cell 22:817) genes can be employed in tk$^-$, hgprt$^-$ or aprt$^-$ cells, respectively. Also, antimetabolite resistance can be used as the basis of selection for dhfr, which confers resistance to methotrexate (Wigler et al., 1980, Natl. Acad. Sci. USA 77:3567; O'Hare et al., 1981, Proc. Natl. Acad. Sci. USA 78:1527); gpt, which confers resistance to mycophenolic acid (Mulligan & Berg, 1981, Proc. Natl. Acad. Sci. USA 78:2072); neo, which confers resistance to the aminoglycoside G-418 (Colberre-Garapin et al., 1981, J. Mol. Biol. 150:1); and hygro, which confers resistance to hygromycin (Santerre et al., 1984, Gene 30:147) genes. Additional selectable genes have been described, namely trpB, which allows cells to utilize indole in place of tryptophan; hisD, which allows cells to utilize histinol in place of histidine (Hartman & Mulligan, 1988, Proc. Natl. Acad. Sci. USA 85:8047); and ODC (ornithine decarboxylase) which confers resistance to the ornithine decarboxylase inhibitor, 2-(difluoromethyl)-DL-ornithine, DFMO (McConlogue L., 1987, In: Current Communications in Molecular Biology, Cold Spring Harbor Laboratory ed.).

5.3. PROTEIN PURIFICATION

The chimeric proteins of the invention can be purified by art-known techniques such as high performance liquid chromatography, ion exchange chromatography, gel electrophoresis, affinity chromatography and the like. The actual conditions used to purify a particular protein will depend, in part, on factors such as net charge, hydrophobicity, hydrophilicity, etc., and will be apparent to those having skill in the art.

For affinity chromatography purification, any antibody which specifically binds the protein may be used. For the production of antibodies, various host animals, including but not limited to rabbits, mice, rats, etc., may be immunized by injection with a chimeric protein or a fragment thereof. The protein may be attached to a suitable carrier, such as bovine serum albumin (BSA), by means of a side chain functional group or linkers attached to a side chain functional group. Various adjuvants may be used to increase the immunological response, depending on the host species, including but not limited to, Freund's (complete and incomplete), mineral gels such as aluminum hydroxide, surface active substances such as lysolecithin, pluronic polyols, polyanions, peptides, oil emulsions, keyhole limpet hemocyanin, dinitrophenol, and potentially useful human adjuvants such as BCG (bacilli Calmette-Guerin) and Corynebacterium parvum.

Monoclonal antibodies to a chimeric protein may be prepared using any technique which provides for the production of antibody molecules by continuous cell lines in culture. These include but are not limited to the hybridoma technique originally described by Koehler and Milstein (1975, Nature 256:495–497), the human B-cell hybridoma technique, (Kosbor et al., 1983, Immunology Today 4:72; Cote et al., 1983, Proc. Natl. Acad. Sci. U.S.A. 80:2026–2030) and the EBV-hybridoma technique (Cole et al., 1985, Monoclonal Antibodies and Cancer Therapy, Alan R. Liss, Inc., pp. 77–96). In addition, techniques developed for the production of "chimeric antibodies" (Morrison et al., 1984, Proc. Natl. Acad. Sci. U.S.A. 81:6851–6855; Neuberger et al., 1984, Nature 312:604–608; Takeda et al., 1985, Nature 314:452–454) by splicing the genes from a mouse antibody molecule of appropriate antigen specificity together with genes from a human antibody molecule of appropriate biological activity can be used. Alternatively, techniques described for the production of single chain antibodies (U.S. Pat. No. 4,946,778) can be adapted to produce chimeric protein-specific single chain antibodies for chimeric protein purification and detection.

5.4. USES OF CHIMERIC PROTEINS

Once a chimeric protein is expressed and purified, its dentity and functional activities can be readily determined by methods well known in the art. For example, antibodies to the two moieties of the protein may be used to identify the protein in Western blot analysis. In addition, the chimeric protein can be tested for specific binding to target cells in binding assays using a fluorescent-labeled or radiolabelled secondary antibody.

5.4.1. IN VITRO AND EX VIVO USES

The chimeric proteins of the invention are useful for targeting specific cell types in a cell mixture, and eliminating the target cells by inducing apoptosis. For example, IL2-Bax may be used to purge IL2R$^+$ leukemic cells in a bone marrow preparation or mobilized peripheral blood prior to infusion of the cells into a recipient following ablative therapy. In addition, this chimeric protein may be used to deplete IL2R$^+$ cells in a donor cell preparation prior to allogeneic or xenogeneic bone marrow transplantation in order to reduce the development of graft-versus-host disease. It can also be used for ex vivo purging of specific cell subsets in any body fluids such as cerebral spinal fluid, pleural fluid and sinovial fluid.

The chimeric protein of the invention is also useful as a diagnostic reagent. For example, IL2-Bax may be used to detect the presence of autoimmune IL2R-expressing cells in a body fluid or to detect the tissue origin of an IL2R$^+$ lymphoma. The binding of a chimeric protein to a target cell can be readily detected by using a secondary antibody specific for the apoptosis-inducing moiety. In that connection, the secondary antibody or the chimeric protein can be linked to a detectable label such as fluorescein, an enzyme or a radioisotope to facilitate the detection of binding of the chimeric protein to a cell.

5.4.2. IN VIVO USES

The chimeric proteins of the invention may be administered to a subject per se or in the form of a pharmaceutical composition for the treatment of cancer, autoimmunity, transplantation rejection, post-traumatic immune responses and infectious diseases by targeting viral antigens such as gp120 of HIV. More specifically, IL2-Bax is useful for eliminating activated IL2R$^+$ cells involved in immune cell-mediated disorder, including lymphoma; autoimmunity, transplantation rejection, graft-versus-host disease, ischemia and stroke. Pharmaceutical compositions comprising the proteins of the invention may be manufactured by means of conventional mixing, dissolving, granulating, dragee-making, levigating, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations which can be used pharmaceutically. Proper formulation is dependent upon the route of administration chosen.

For topical administration the proteins of the invention may be formulated as solutions, gels, ointments, creams, suspensions, etc. as are well-known in the art.

Systemic formulations include those designed for administration by injection, e.g. subcutaneous, intravenous, intramuscular, intrathecal or intraperitoneal injection, as well as those designed for transdermal, transmucosal, inhalation, oral or pulmonary administration.

For injection, the proteins of the invention may be formulated in aqueous solutions, preferably in physiologically compatible buffers such as Hanks's solution, Ringer's solution, or physiological saline buffer. The solution may contain formulatory agents such as suspending, stabilizing and/or dispersing agents.

Alternatively, the proteins may be in powder form for constitution with a suitable vehicle, e.g., sterile pyrogen-free water, before use.

For transmucosal administration, penetrants appropriate to the barrier to be permeated are used in the formulation. Such penetrants are generally known in the art.

For oral administration, the proteins can be readily formulated by combining the proteins with pharmaceutically acceptable carriers well known in the art. Such carriers enable the proteins of the invention to be formulated as tablets, pills, dragees, capsules, liquids, gels, syrups, slurries, suspensions and the like, for oral ingestion by a patient to be treated. For oral solid formulations such as, for example, powders, capsules and tablets, suitable excipients include fillers such as sugars, e.g. lactose, sucrose, mannitol and sorbitol; cellulose preparations such as maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP); granulating agents; and binding agents. If desired, disintegrating agents may be added, such as the cross-linked polyvinylpyrrolidone, agar, or alginic acid or a salt thereof such as sodium alginate.

If desired, solid dosage forms may be sugar-coated or enteric-coated using standard techniques.

For oral liquid preparations such as, for example, suspensions, elixirs and solutions, suitable carriers, excipients or diluents include water, glycols, oils, alcohols, etc. Additionally, flavoring agents, preservatives, coloring agents and the like may be added.

For buccal administration, the proteins may take the form of tablets, lozenges, etc. formulated in conventional manner.

For administration by inhalation, the proteins for use according to the present invention are conveniently delivered in the form of an aerosol spray from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of gelatin for use in an inhaler or insufflator may be formulated containing a powder mix of the protein and a suitable powder base such as lactose or starch.

The proteins may also be formulated in rectal or vaginal compositions such as suppositories or retention enemas, e.g, containing conventional suppository bases such as cocoa butter or other glycerides.

In addition to the formulations described previously, the proteins may also be formulated as a depot preparation. Such long acting formulations may be administered by implantation (for example subcutaneously or intramuscularly) or by intramuscular injection. Thus, for example, the proteins may be formulated with suitable polymeric or hydrophobic materials (for example as an emulsion in an acceptable oil) or ion exchange resins, or as sparingly soluble derivatives, for example, as a sparingly soluble salt.

Alternatively, other pharmaceutical delivery systems may be employed. Liposomes and emulsions are well known examples of delivery vehicles that may be used to deliver proteins of the invention. Certain organic solvents such as dimethylsulfoxide also may be employed, although usually at the cost of greater toxicity. Additionally, the proteins may be delivered using a sustained-release system, such as semipermeable matrices of solid polymers containing the therapeutic agent. Various of sustained-release materials have been established and are well known by those skilled in the art. Sustained-release capsules may, depending on their chemical nature, release the proteins for a few weeks up to over 100 days. Depending on the chemical nature and the biological stability of the chimeric protein, additional strategies for protein stabilization may be employed.

As the proteins of the invention may contain charged side chains or termini, they may be included in any of the above-described formulations as the free acids or bases or as pharmaceutically acceptable salts. Pharmaceutically acceptable salts are those salts which substantially retain the biologic activity of the free bases and which are prepared by reaction with inorganic acids. Pharmaceutical salts tend to be more soluble in aqueous and other protic solvents than are the corresponding free base forms.

5.4.3. EFFECTIVE DOSAGES

The proteins of the invention will generally be used in an amount effective to achieve the intended purpose. For use to treat or prevent a disease condition, the proteins of the invention, or pharmaceutical compositions thereof, are administered or applied in a therapeutically effective amount. A therapeutically effective amount is an amount effective to ameliorate or prevent the symptoms, or prolong the survival of, the patient being treated. Determination of a therapeutically effective amount is well within the capabilities of those skilled in the art, especially in light of the detailed disclosure provided herein.

For systemic administration, a therapeutically effective dose can be estimated initially from in vitro assays. For example, a dose can be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the proteins which are sufficient to maintain therapeutic effect. Usual patient dosages for administration by injection range from about 0.1 to 5 mg/kg/day, preferably from about 0.5 to 1 mg/kg/day. Therapeutically effective serum levels may be achieved by administering multiple doses each day.

In cases of local administration or selective uptake, the effective local concentration of the proteins may not be related to plasma concentration. One having skill in the art will be able to optimize therapeutically effective local dosages without undue experimentation.

The amount of protein administered will, of course, be dependent on the subject being treated, on the subject's weight, the severity of the affliction, the manner of administration and the judgment of the prescribing physician.

The therapy may be repeated intermittently while symptoms detectable or even when they are not detectable. The therapy may be provided alone or in combination with other drugs. In the case of autoimmune disorders, the drugs that may be used in combination with IL2-Bax of the invention include, but are not limited to, steroid and non-steroid anti-inflammatory agents.

5.4.4. TOXICITY

Preferably, a therapeutically effective dose of the chimeric proteins described herein will provide therapeutic benefit without causing substantial toxicity.

Toxicity of the proteins described herein can be determined by standard pharmaceutical procedures in cell cultures or experimental animals, e.g., by determining the $LD_{50}$ (the dose lethal to 50% of the population) or the $LD_{100}$ (the dose lethal to 100% of the population). The dose ratio between toxic and therapeutic effect is the therapeutic index. Proteins which exhibit high therapeutic indices are preferred. The data obtained from these cell culture assays and animal studies can be used in formulating a dosage range that is not toxic for use in human. The dosage of the proteins described herein lies preferably within a range of circulating concentrations that include the effective dose with little or no toxicity. The dosage may vary within this range depending upon the dosage form employed and the route of administration utilized. The exact formulation, route of administration and dosage can be chosen by the individual physician in view of the patient's condition. (See, e.g., Fingl et al., 1975, In: *The Pharmacological Basis of Therapeutics*, Ch.1, p.1).

The invention having been described, the following examples are offered by way of illustration and not limitation.

6. EXAMPLE

Production of a Chimeric Protein that Induced $IL2R^+$ Cell-Specific Apoptosis

6.1. MATERIALS AND METHODS

6.1.1. CONSTRUCTION OF IL2-BAX CODING SEQUENCE

A plasmid for the expression of IL2-Bax chimeric protein under the control of the T7 promoter was constructed as shown in FIG. 1. pHL906 which carried the fusion gene IL2-PE40 was cut with HindIII and PpuMI to remove the PE sequence, and the vector fragment was eluted (Fishman et al., 1994, Biochem. 33:6235–6243). A cDNA encoding human Bax-α was obtained by reverse transcription-polymerase chain reaction (RT-PCR), using RNA isolated from fresh human lymphocytes. Total RNA was isolated and was reverse transcribed into first strand cDNA, using the reverse transcription system (Promega, USA) under conditions recommended by the manufacturer. The cDNA was diluted to a total volume of 1 ml with 10 mM Tris-HCl pH 7.6, 1 mM EDTA and stored at 4° C. The Bax-encoding fragment was generated by PCR using this cDNA and a pair of synthetic oligonucleotide primers: 5' CGCAAT-TCAAGCTTTGGACGGGTCCGGGGGA 3' (SEQ ID NO:3) (sense) and 5' CGGAATTCAGGTCGTTCAGC-CCATCTTCTTC 3' (SEQ ID NO:4)

(antisense) covering the entire coding region. The reaction mixture was incubated in a DNA thermal cycler (MJ Research Inc., Watertown, Mass.) for 33 cycles. Each cycle consisted of 1 min. at 95° C., 1 min. at 65° C. and 2 min. at 72° C. The Bax-encoding fragment was digested with EcoRI and HindIII enzymes and ligated with the pHL906 vector. The resulting plasmid, designated pSY1, contained the human IL2 coding sequence fused to the 5' end of the human Bax coding sequence. The plasmid was confirmed by restriction endonuclease digestion and DNA sequence analysis. The nucleotide and deduced amino acid sequences (SEQ ID NOS:1 and 2) of the chimeric molecule referred to as IL2-Bax are disclosed in FIG. 2.

6.1.2. PROTEIN EXPRESSION AND PARTIAL PURIFICATION

The pSY1 plasmid containing the fused coding sequences was transformed into *E. coli* strain BL21 (λDE3) and the IL2-Bax chimeric protein was expressed. A pellet of expressing cells was suspended in 50 mM Tris-HCl pH 8.0, 1 mM EDTA containing 0.2 mg/ml lysozyme, sonicated (three 30-s bursts) and centrifuged at 30,000×g for 30 min. The supernatant (soluble fraction) was removed and kept for analysis. The pellet was denatured in one of three extraction buffers:

1) Extraction buffer A: 6 M Guanidine-HCl, 0.1 M Tris-HCl pH 8.6, 1 mM EDTA, 0.05 M NaCl, and 10 mM DTT, and stirred for 30 min. at 4° C. The suspension was cleared by centrifugation at 30,000×g for 15 min. and the pellet discarded. The protein solution was diluted 1:100 in refolding buffer (50 mM Tris-HCl, pH 8.0, 1 mM EDTA, 0.25 M NaCl, 0.25 M L-arginine, and 5 mM dithiothreitol) and kept at 4° C. for 48 h. The refolded protein solution was dialyzed against phosphate-buffered saline (PBS).

2) Extraction buffer B: 20 mM Tris-HCl pH 7.4, 150 mM NaCl, 1 mM EDTA, 1% NP-40, 1% deoxycholic acid, 0.1% SDS. Before testing its activity, the fraction was dialyzed against PBS.

3) Extraction buffer C: 8 M Urea, 50 mM Tris HCl pH 8.0, 1 mM EDTA, 10 mM DTT (v/w 1:1) for 1 hr, centrifuged at 35,000×g for 15 min. The supernatant was diluted 1:100 with refolding buffer (see above) without dithiothreitol.

The protein profile of various fractions (soluble fraction, insoluble fraction-treated in three different protocols) were characterized by gel electrophoresis (FIG. 3).

6.1.3. WESTERN BLOT ANALYSIS

The electrophoresis samples were transferred onto nitrocellulose and immunoblotted as described (Fishman and Lorberboum-Galski, 1997, Eur. J. Immunol. 27:486–494). The ECL detection kit (Amersham, Bukinghamshire, UK) was used according to the manufacturer's instructions. A protein extract from MCF-7 cells (breast carcinoma cell line), known to express the Bax protein, was used as a positive control. Anti-human Bax was obtained from Pharmingen (San Diego, Calif.) and used at a dilution of 1:2,500. Anti-human IL2 was obtained from Endogen and used at a dilution of 1:5,000.

6.1.4. ASSAY FOR IDENTIFYING APOPTOTIC CELLS

Human peripheral blood lymphocytes from healthy donors were separated using Ficoll-Isopaque gradient (1.077) (Pharmacia) and used immediately. Lymphocytes were cultured in 5% $CO_2$ in air in RPMI 1640 medium supplemented with 10% fetal calf serum, 200 µg/ml L-glutamate, 50 µg/ml penicillin, 50 µg/ml streptomycin, 50 µg/ml glutamine and $5 \times 10^{-5}$ M 2-β mercaptoethanol. Increasing concentrations of IL2-Bax (insoluble fraction, 6M Gu-HCl treated) were added to the lymphocytes for 22 hr. Cells were then stained with:

A. Propidium Iodide (PI, 3.5 µg/ml)

B. Propidium Iodide with a detergent for measuring cell cycle (0.7 ml of the PI buffer: 50 µg/ml PI, 0.1% Nacitrate, 0.1% Tritonx100, were added to a cell pellet of ~$10^6$ cells). Cells were then analyzed by FACS.

HUT102 cells (target T cells) and CEM cells (non-target T cells) were incubated overnight with increasing concentrations of IL2-Bax. The 200×g centrifuged cell pellet was fixed in 2 ml cold 70% ethanol at 4° C. for 60 min. The cells were then centrifuged, washed in 1 ml PBS and resuspended in 0.5 ml PBS. 0.5 ml RNAse (Type I-A, Sigma, St. Louis, Mo., 1 mg/ml in PBS) was added to the sample, followed by gentle mixing with 1 ml PI (Sigma, 100 µg/ml PBS) solution. The mixed cells were incubated in the dark at room temperature for 15 min. and kept at 4° C. in the dark until measured. The PI fluorescence of the individual nuclei was measured using FACS flow cytometer. The forward scatter and side scatter of particles were simultaneously measured. Cell debris were excluded from analysis by appropriately raising the forward scatter threshold (Nicoletti et al., 1991, J. Immunol. Meth. 139:271–279).

6.1.5. CYTOTOXICITY ASSAY

Cells ($10^4$ in 0.2 ml culture medium) were seeded in 96-well microplates, followed by the addition of various concentrations of the chimeric protein (diluted with 0.25% BSA in PBS). After a 24 hour incubation, [$^3$H] leucine (2–5 uci/well) were added for 6–13 hr. The plates were then stored at −70° C. for several hours, followed by quick thawing at 37° C. This step was omitted with targets cells growing in suspension. The cells were harvested on filters and the incorporated radioactivity was measured with a β counter. Results were expressed as the percent incorporation of the control experiments in which the cells were not exposed to any protein. All assays were carried out in triplicates.

6.2. RESULTS

An expression plasmid encoding an IL2-Bax chimeric protein was constructed under the control of the T7 promoter. The plasmid was expressed in *E. coli* and the chimeric protein was extracted. The protein was further characterized by Western blot analysis using antibodies against Bax and IL2 (FIG. 4). The chimeric protein reacted with the antibodies to Bax and to IL2, confirming the cloning and production of in-frame full-length IL2-Bax chimeric protein.

The cytotoxic activity of the IL2-Bax chimeric protein was tested on HUT102 and MT-1 cells (human T-cell lines), and 2B4 cells (mouse T-cells); all known to express the high affinity receptor for IL2, by a quantitative assay, in which inhibition of protein synthesis was measured. The soluble and insoluble fractions generated from treatment under three different conditions were tested in cytotoxicity assays as described by Lorberboum-Galski et al. (1988, J. Biol. Chem. 263:18650–18656). As shown in FIG. 5A, all three IL2R-expressing cell lines were responsive to the chimeric protein in a dose dependent manner, although with different sensitivities. This may be attributed to the different number of IL2R expressed on each cell line. The insoluble fraction treated with ether extraction buffer containing Gu-HCl or SDS exhibited the highest activity toward the various cells. Therefore, further experiments were performed with mainly the partially purified fractions (insoluble fraction extracted with Gu-HCl or SDS). In all experiments IL2-PE chimeric proteins, previously shown to be cytotoxic to IL2R$^+$ cells, were used as positive control.

Figure 5B:
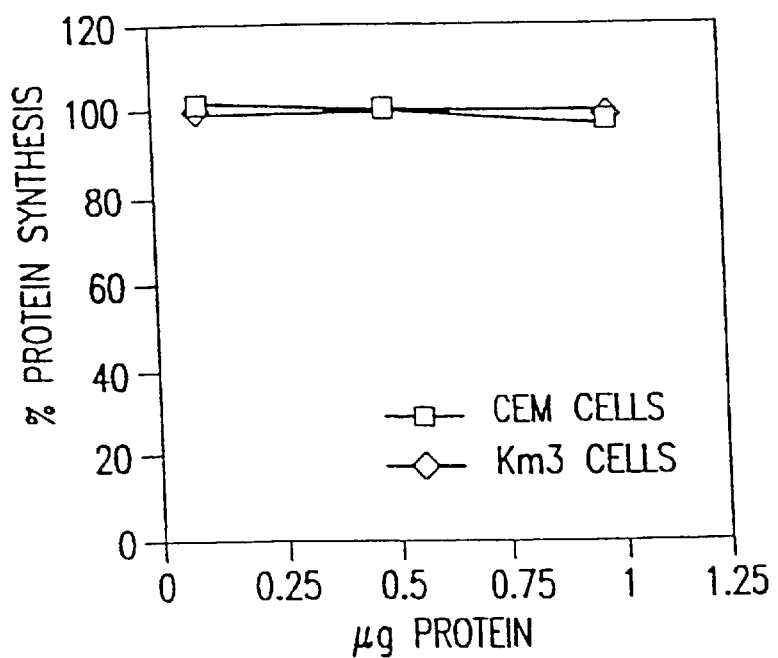
Figure 6B:
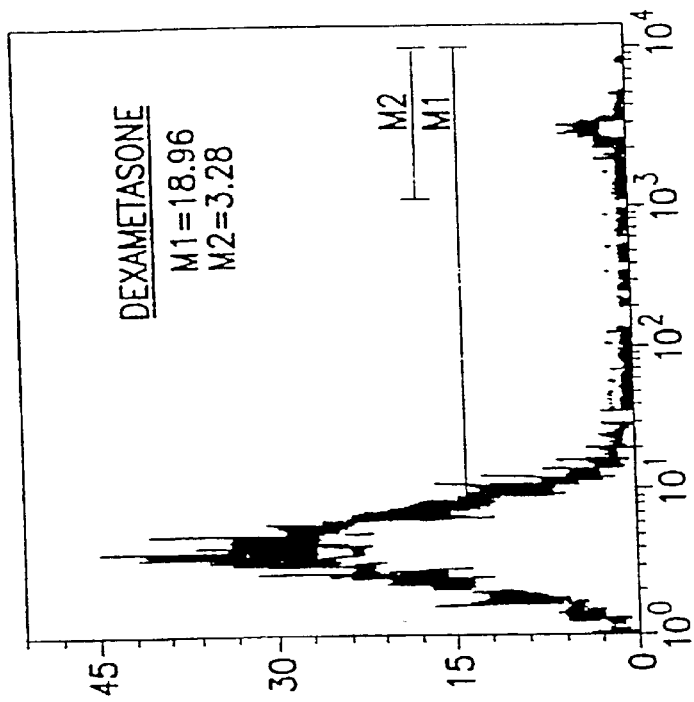
Figure 6A:
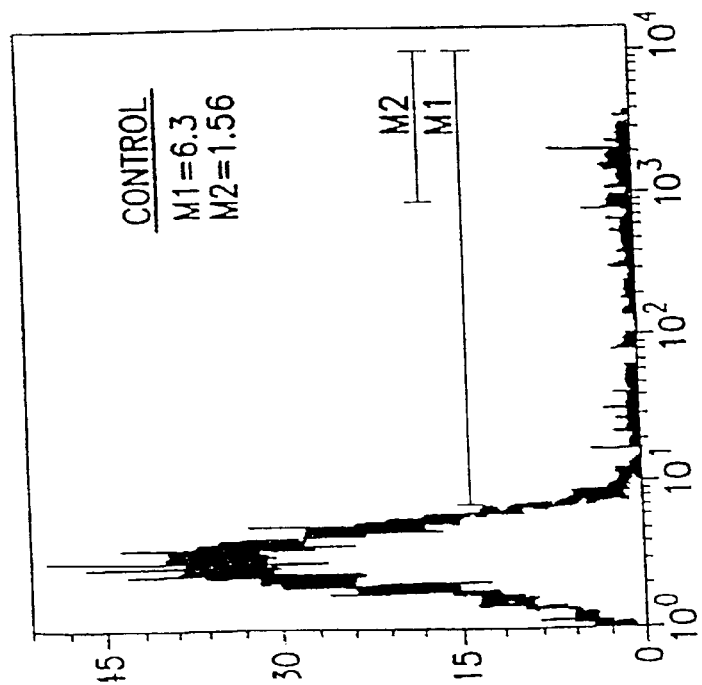
Figure 6D:
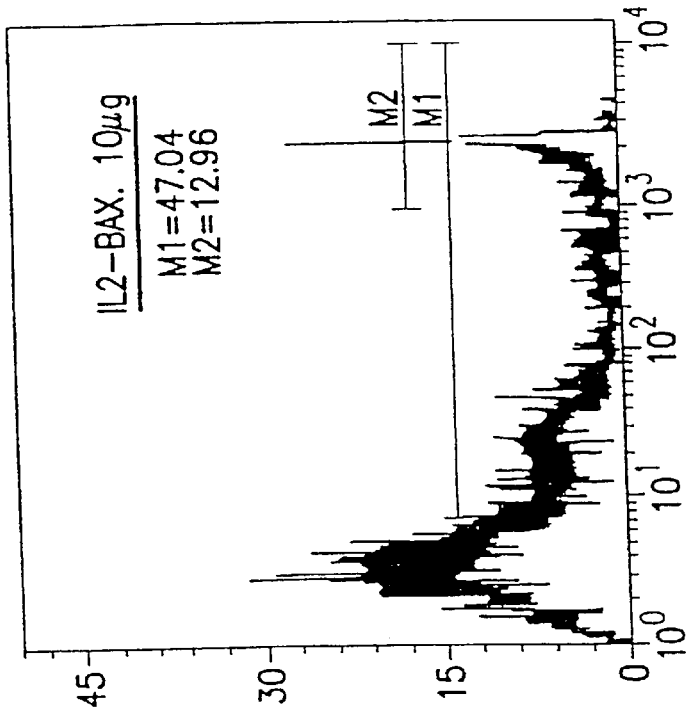
Figure 6C:
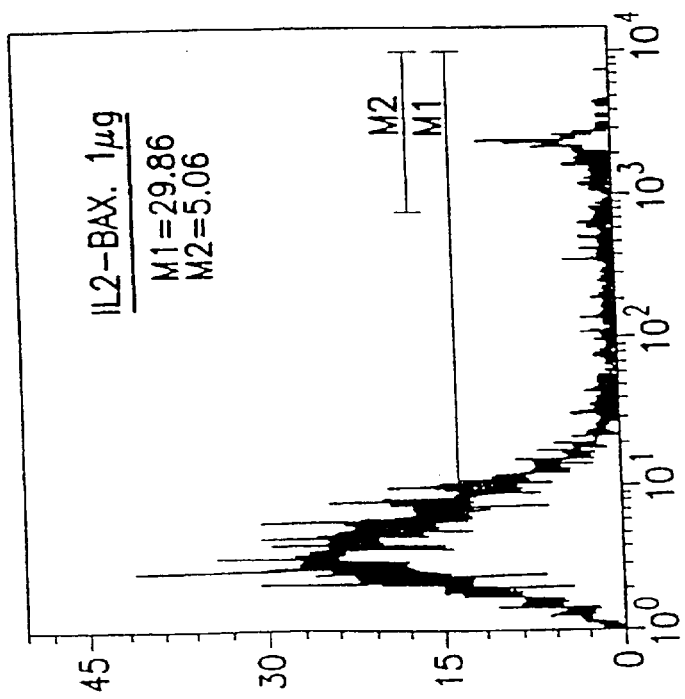

The effects of IL2-Bax were also tested on various IL2R negative cells: CEM cells (a human T-cell line lacking the IL2R) and Km3 (a human non-T, non-B stem cell line). FIG. 5B shows that these cell lines were unaffected by the IL2-Bax chimeric protein. Since the fraction treated with Gu-HCl was active without any non-specific cytotoxicity, this fraction was further used in subsequent experiments.

The ability of IL2-Bax to induce apoptosis in IL2R$^+$ cells was determined in an apoptosis assay. FIGS. 6A–6D shows an increase of apoptotic cells in a freshly isolated lymphocyte population treated with IL2-Bax, and the effects of the chimeric protein were dose dependent. The apoptotic cells ranged from 2% to 14% (Table 1A, B) of the total cell population (FIGS. 7A–7C). In that regard, it should be noted that freshly isolated lymphocytes from healthy donors usually contain only low levels of cells expressing the IL2R, thus the percentage of cells expected to be targeted by IL2-Bax in fresh lymphocytes is low.

Dexamethasone ($10^{-7}$ M), a known inducer for apoptosis in various cells, was used in all experiments to follow apoptosis. However, it is well known that various cells respond differently to, if at all, to this reagent. Dexamethasone was also shown to be a weak inducer of apoptosis in fresh lymphocytes (FIG. 6B). 2B4 cells, known to react very strongly to this agent were used as control cells to detect apoptosis. In conclusion, recombinant chimeric protein IL2-Bax was specifically cytotoxic to IL2R$^+$ cells, but did not affect IL2R$^-$ cells. Furthermore, the cytotoxic effects of the chimeric protein were mediated by an induction of apoptosis, as evidenced by its ability to induce programmed cell death in freshly isolated human lymphocytes.

TABLE 1

Effect of IL2-Bax on Fresh Lymphocytes Analyzed by FACS

| Treatment | M1 | M2 | M1-2 |
|---|---|---|---|
| A. Experiment No. 1 | | | |
| control | 7.1 | 1.9 | 5.2 |
| dexamethasone | 9.5 | 2.8 | 6.7 |
| IL2-Bax, 1 µg | 17.5 | 4 | 13.5 |
| IL2-Bax, 5 µg | 24.3 | 4.3 | 20 |
| IL2-Bax, 10 µg | 42.1 | 9.1 | 35 |

| Treatment | UL | UR | UL + UR |
|---|---|---|---|
| B. Experiment No. 2 | | | |
| control | 2.36 | 2.12 | 4.48 |
| IL2-Bax, 1 µg | 4.98 | 5.56 | 10.54 |
| IL2-Bax, 10 µg | 14.71 | 16.84 | 31.55 |

Each M1 or M2 values are the mean of duplicates.
Each UL or UR value is the mean of duplicates.

FIGS. 8A–8E demonstrates the increase of an apoptotic-cell population in HUT102 cells exposed to IL2-Bax in a dose dependent manner (M1 values represent the sub-G1 apoptotic-cell population). At the highest concentration tested, IL2-Bax induced a 3.6-fold increase in the percentage of the apoptotic-cell population. In contrast, CEM cells which lacked IL2R expression did not show an increase in the apoptotic cell population (FIGS. 9A–9C), confirming the specificity of the effects of IL2-Bax.

The present invention is not to be limited in scope by the exemplified embodiments which are intended as illustrations of single aspects of the invention and any sequences which are functionally equivalent are within the scope of the invention. Indeed, various modifications of the invention in addition to those shown and described herein will become apparent to those skilled in the art from the foregoing description and accompanying drawings. Such modifications are intended to fall within the scope of the appended claims.

All publications cited herein are incorporated by reference in their entirety.

What is claimed is:

1. A chimeric protein comprising a cell-specific targeting moiety and an apoptosis-inducing moiety wherein the cell-specific targeting moiety is a cytokine, a growth factor, a hormone, or an antibody or a fragment thereof, and the apoptosis-inducing moiety is a pro-apoptotic member of the Bcl-2 family selected from the group consisting of Bax-α, Bak, Bcl-$X_S$, Bad, Bid, Bik, Erk, and Bok.

2. The chimeric protein of claim 1 in which the apoptosis-inducing moiety is Bax or a domain thereof having an apoptosis-inducing activity.

3. The chimeric protein of claim 1 in which the cell-specific targeting moiety binds interleukin 2 receptor-expressing cells.

4. The chimeric protein of claim 1 in which the cell-specific targeting moiety is an interleukin.

5. The chimeric protein of claim 4 in which the cell-specific targeting moiety is an interleukin 2.

6. The chimeric protein of claim 1 in which the cell-specific targeting moiety is interleukin 2 and the apoptosis-inducing moiety is Bax-α.

7. The chimeric protein of claim 1 in which the antibody is a single chain antibody.

8. The chimeric protein of claim 1 in which the antibody fragment is an Fc fragment of an IgE antibody.

9. The chimeric protein of claim 1 which is produced by a recombinant DNA method.

10. The chimeric protein of claim 1 which is produced by a chemical conjugation method.

11. The chimeric protein of claim 1 in which the two moieties are connected by a polylinker.

12. A pharmaceutical composition comprising a chimeric protein of any one of claims 1, 2, 3, 6, 7, 8, and 9–11.

* * * * *

UNITED STATES PATENT AND TRADEMARK OFFICE
CERTIFICATE OF CORRECTION

PATENT NO. : 6,645,490 B2
DATED : November 11, 2003
INVENTOR(S) : Shai Yarkoni et al.

It is certified that error appears in the above-identified patent and that said Letters Patent is hereby corrected as shown below:

Column 28,
Line 57, "1, 2, 3, 6, 7, 8 and 9-11." should read -- 1-11. --.

Signed and Sealed this

Twenty-fourth Day of August, 2004

JON W. DUDAS
*Director of the United States Patent and Trademark Office*

SEQUENCE LISTING

```
<160> NUMBER OF SEQ ID NOS: 10

<210> SEQ ID NO 1
<211> LENGTH: 996
<212> TYPE: DNA
<213> ORGANISM: Homo sapiens
<220> FEATURE:
<221> NAME/KEY: CDS
<222> LOCATION: (1)...(993)

<400> SEQUENCE: 1 atg gca gat cct act tca agt tct aca aag aaa aca cag cta caa ctg        48
Met Ala Asp Pro Thr Ser Ser Ser Thr Lys Lys Thr Gln Leu Gln Leu
  1               5                  10                  15 gag cat tta ctg ctg gat tta cag atg att ttg aat gga att aat aat        96
Glu His Leu Leu Leu Asp Leu Gln Met Ile Leu Asn Gly Ile Asn Asn
             20                  25                  30 tac aag aat ccc aaa ctc acc agg atg ctc aca ttt aag ttt tac atg       144
Tyr Lys Asn Pro Lys Leu Thr Arg Met Leu Thr Phe Lys Phe Tyr Met
         35                  40                  45 ccc aag aag gcc aca gaa ctg aaa cat ctt cag tgt cta gaa gaa gaa       192
Pro Lys Lys Ala Thr Glu Leu Lys His Leu Gln Cys Leu Glu Glu Glu
     50                  55                  60 ctc aaa cct ctg gag gaa gtg cta aat tta gct caa agc aaa aac ttt       240
Leu Lys Pro Leu Glu Glu Val Leu Asn Leu Ala Gln Ser Lys Asn Phe
 65                  70                  75                  80 cac tta aga ccc agg gac tta atc agc aat atc aac gta ata gtt ctg       288
His Leu Arg Pro Arg Asp Leu Ile Ser Asn Ile Asn Val Ile Val Leu
                 85                  90                  95 gaa cta aag gga tct gaa aca aca ttc atg tgt gaa tat gct gat gag       336
Glu Leu Lys Gly Ser Glu Thr Thr Phe Met Cys Glu Tyr Ala Asp Glu
            100                 105                 110 aca gca acc att gta gaa ttt ctg aac aga tgg att acc ttt tgt caa       384
Thr Ala Thr Ile Val Glu Phe Leu Asn Arg Trp Ile Thr Phe Cys Gln
        115                 120                 125 agc atc atc tca aca atc ccc gag ggc gaa gct ttg gac ggg tcc ggg       432
Ser Ile Ile Ser Thr Ile Pro Glu Gly Glu Ala Leu Asp Gly Ser Gly
    130                 135                 140 gag cag ccc aga ggc ggg ggg ccc acc agc tct gag cag atc atg aag       480
Glu Gln Pro Arg Gly Gly Gly Pro Thr Ser Ser Glu Gln Ile Met Lys
145                 150                 155                 160 aca ggg gcc ctt ttg ctt cag ggt ttc atc cag gat cga gca ggg cga       528
Thr Gly Ala Leu Leu Leu Gln Gly Phe Ile Gln Asp Arg Ala Gly Arg
                165                 170                 175 atg ggg ggg gag gca ccc gag ctg gcc ctg gac ccg gtg cct cag gat       576
Met Gly Gly Glu Ala Pro Glu Leu Ala Leu Asp Pro Val Pro Gln Asp
            180                 185                 190 gcg tcc acc aag aag ctg agc gag tgt ctc aag cgc atc ggg gac gaa       624
Ala Ser Thr Lys Lys Leu Ser Glu Cys Leu Lys Arg Ile Gly Asp Glu
        195                 200                 205
```

```
ctg gac agt aac atg gag ctg cag agg atg att gcc gcc gtg gac aca      672
Leu Asp Ser Asn Met Glu Leu Gln Arg Met Ile Ala Ala Val Asp Thr
    210                 215                 220 gac tcc ccc cga gag gtc ttt ttc cga gtg gca gct gac atg ttt tct      720
Asp Ser Pro Arg Glu Val Phe Phe Arg Val Ala Ala Asp Met Phe Ser
225                 230                 235                 240 gac ggc aac ttc aac tgg ggc cgg gtt gtc gcc ctt ttc tac ttt gcc      768
Asp Gly Asn Phe Asn Trp Gly Arg Val Val Ala Leu Phe Tyr Phe Ala
                245                 250                 255 agc aaa ctg gtg ctc aag gcc ctg tgc acc aag gtg ccg gaa ctg atc      816
Ser Lys Leu Val Leu Lys Ala Leu Cys Thr Lys Val Pro Glu Leu Ile
            260                 265                 270 aga acc atc atg ggc tgg aca ttg gac ttc ctc cgg gag cgg ctg ttg      864
Arg Thr Ile Met Gly Trp Thr Leu Asp Phe Leu Arg Glu Arg Leu Leu
        275                 280                 285 ggc tgg atc caa gac cag ggt ggt tgg gac ggc ctc ctc tcc tac ttt      912
Gly Trp Ile Gln Asp Gln Gly Gly Trp Asp Gly Leu Leu Ser Tyr Phe
    290                 295                 300 ggg acg ccc acg tgg cag acc gtg acc atc ttt gtg gcg gga gtg ctc      960
Gly Thr Pro Thr Trp Gln Thr Val Thr Ile Phe Val Ala Gly Val Leu
305                 310                 315                 320 acc gcc tcg ctc acc atc tgg aag aag atg ggc tga                      996
Thr Ala Ser Leu Thr Ile Trp Lys Lys Met Gly
                325                 330
```

<210> SEQ ID NO 2
<211> LENGTH: 331
<212> TYPE: PRT
<213> ORGANISM: Homo sapiens

<400> SEQUENCE: 2

```
Met Ala Asp Pro Thr Ser Ser Thr Lys Lys Thr Gln Leu Gln Leu
 1               5                  10                  15

Glu His Leu Leu Leu Asp Leu Gln Met Ile Leu Asn Gly Ile Asn Asn
                20                  25                  30

Tyr Lys Asn Pro Lys Leu Thr Arg Met Leu Thr Phe Lys Phe Tyr Met
            35                  40                  45

Pro Lys Lys Ala Thr Glu Leu Lys His Leu Gln Cys Leu Glu Glu Glu
        50                  55                  60

Leu Lys Pro Leu Glu Glu Val Leu Asn Leu Ala Gln Ser Lys Asn Phe
65                  70                  75                  80

His Leu Arg Pro Arg Asp Leu Ile Ser Asn Ile Asn Val Ile Val Leu
                85                  90                  95

Glu Leu Lys Gly Ser Glu Thr Thr Phe Met Cys Glu Tyr Ala Asp Glu
                100                 105                 110

Thr Ala Thr Ile Val Glu Phe Leu Asn Arg Trp Ile Thr Phe Cys Gln
            115                 120                 125

Ser Ile Ile Ser Thr Ile Pro Glu Gly Glu Ala Leu Asp Gly Ser Gly
        130                 135                 140

Glu Gln Pro Arg Gly Gly Pro Thr Ser Ser Glu Gln Ile Met Lys
145                 150                 155                 160

Thr Gly Ala Leu Leu Leu Gln Gly Phe Ile Gln Asp Arg Ala Gly Arg
                165                 170                 175

Met Gly Gly Glu Ala Pro Glu Leu Ala Leu Asp Pro Val Pro Gln Asp
                180                 185                 190

Ala Ser Thr Lys Lys Leu Ser Glu Cys Leu Lys Arg Ile Gly Asp Glu
            195                 200                 205
```

```
Leu Asp Ser Asn Met Glu Leu Gln Arg Met Ile Ala Ala Val Asp Thr
    210                 215                 220

Asp Ser Pro Arg Glu Val Phe Phe Arg Val Ala Ala Asp Met Phe Ser
225                 230                 235                 240

Asp Gly Asn Phe Asn Trp Gly Arg Val Val Ala Leu Phe Tyr Phe Ala
                245                 250                 255

Ser Lys Leu Val Leu Lys Ala Leu Cys Thr Lys Val Pro Glu Leu Ile
                260                 265                 270

Arg Thr Ile Met Gly Trp Thr Leu Asp Phe Leu Arg Glu Arg Leu Leu
            275                 280                 285

Gly Trp Ile Gln Asp Gln Gly Gly Trp Asp Gly Leu Leu Ser Tyr Phe
        290                 295                 300

Gly Thr Pro Thr Trp Gln Thr Val Thr Ile Phe Val Ala Gly Val Leu
305                 310                 315                 320

Thr Ala Ser Leu Thr Ile Trp Lys Lys Met Gly
                325                 330
```

<210> SEQ ID NO 3
<211> LENGTH: 31
<212> TYPE: DNA
<213> ORGANISM: Homo sapiens

<400> SEQUENCE: 3
cgcaattcaa gctttggacg ggtccggggg a                                31

<210> SEQ ID NO 4
<211> LENGTH: 31
<212> TYPE: DNA
<213> ORGANISM: Homo sapiens

<400> SEQUENCE: 4
cggaattcag gtcgttcagc ccatcttctt c                                31

<210> SEQ ID NO 5
<211> LENGTH: 5
<212> TYPE: PRT
<213> ORGANISM: Artificial Sequence
<220> FEATURE:
<223> OTHER INFORMATION: Flexible polylinker

<400> SEQUENCE: 5

```
Gly Gly Gly Gly Ser
 1               5
```

<210> SEQ ID NO 6
<211> LENGTH: 14
<212> TYPE: PRT
<213> ORGANISM: Artificial Sequence
<220> FEATURE:
<223> OTHER INFORMATION: Linker

<400> SEQUENCE: 6

```
Glu Gly Lys Ser Ser Gly Ser Gly Ser Glu Ser Lys Val Asp
 1               5                   10
```

<210> SEQ ID NO 7
<211> LENGTH: 18
<212> TYPE: PRT
<213> ORGANISM: Artificial Sequence
<220> FEATURE:
<223> OTHER INFORMATION: Linker

<400> SEQUENCE: 7

```
Lys Glu Ser Gly Ser Val Ser Ser Glu Gln Leu Ala Gln Phe Arg Ser
 1               5                  10                  15

Leu Asp

<210> SEQ ID NO 8
<211> LENGTH: 5
<212> TYPE: PRT
<213> ORGANISM: Artificial Sequence
<220> FEATURE:
<223> OTHER INFORMATION: Conserved active-site motif
<221> NAME/KEY: SITE
<222> LOCATION: (4)...(4)
<223> OTHER INFORMATION: Xaa = Arg or Gly

<400> SEQUENCE: 8

Gln Ala Cys Xaa Gly
 1               5

<210> SEQ ID NO 9
<211> LENGTH: 14
<212> TYPE: DNA
<213> ORGANISM: Artificial Sequence
<220> FEATURE:
<223> OTHER INFORMATION: Portion of pSY1 plasmid

<400> SEQUENCE: 9
aagctttgga cggg                                                14

<210> SEQ ID NO 10
<211> LENGTH: 13
<212> TYPE: DNA
<213> ORGANISM: Artificial Sequence
<220> FEATURE:
<223> OTHER INFORMATION: Portion of pSY1 plasmid

<400> SEQUENCE: 10
ggctgaagga cct                                                 13
```